(12) United States Patent
Bake et al.

(10) Patent No.: US 11,065,011 B2
(45) Date of Patent: Jul. 20, 2021

(54) TOOLS FOR ASSISTING IN OSTEOTOMY PROCEDURES, AND METHODS FOR DESIGNING AND MANUFACTURING OSTEOTOMY TOOLS

(71) Applicant: EPISURF IP-MANAGEMENT AB, Stockholm (SE)

(72) Inventors: Nina Bake, Lidingö (SE); Richard Lilliestråle, Stockholm (SE); Leif Ryd, Malmö (SE); Katarina Flodström, Danderyd (SE); Jonas Jägerback, Sundbyberg (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 89 days.

(21) Appl. No.: 15/871,376

(22) Filed: Jan. 15, 2018

(65) Prior Publication Data
US 2018/0153558 A1 Jun. 7, 2018

Related U.S. Application Data

(63) Continuation-in-part of application No. 15/526,539, filed as application No. PCT/EP2014/074533 on Nov. 13, 2014, now Pat. No. 10,327,785.

(51) Int. Cl.
*A61F 2/42* (2006.01)
*A61F 2/30* (2006.01)
(Continued)

(52) U.S. Cl.
CPC ............ *A61B 17/151* (2013.01); *A61B 17/15* (2013.01); *A61B 17/1775* (2016.11);
(Continued)

(58) Field of Classification Search
CPC ... A61B 17/15; A61B 17/155; A61B 17/1764; A61B 34/20; A61B 17/17; A61B 2034/107; A61B 2034/2055; A61B 17/157; A61B 2034/2065; A61B 17/1739; A61B 17/1775; A61B 17/16; A61B 17/1615; A61B 17/1659; A61F 2/389; A61F 2002/4633; A61F 2/4684; A61F 2/4606;
(Continued)

(56) References Cited

U.S. PATENT DOCUMENTS 6,673,116 B2 1/2004 Reiley
2008/0097617 A1 4/2008 Fellinger et al.
(Continued)

FOREIGN PATENT DOCUMENTS

WO WO-2014/020562 A1 2/2014
WO WO-2017/070318 A1 4/2017

OTHER PUBLICATIONS

Office Communication issued in international application No. PCT/EP2018/050889, dated Oct. 16, 2018.

*Primary Examiner* — Ann Schillinger
(74) *Attorney, Agent, or Firm* — Faegre Drinker Biddle & Reath LLP

(57) ABSTRACT

The present invention relates to a surgical kit, a saw guide and other related tools used in the osteotomy for temporary removal of a piece of a first bone structure to gain temporary access for treatment of defects of a second bone structure, as well as methods for designing and manufacturing said tools.

29 Claims, 24 Drawing Sheets

(51) Int. Cl.
*A61B 17/15* (2006.01)
*A61B 17/16* (2006.01)
*A61B 17/17* (2006.01)
*A61B 90/00* (2016.01)

(52) U.S. Cl.
CPC ...... *A61F 2/4202* (2013.01); *A61B 2090/062* (2016.02); *A61F 2/30942* (2013.01); *A61F 2002/30299* (2013.01); *A61F 2002/30878* (2013.01); *A61F 2002/4207* (2013.01)

(58) Field of Classification Search
CPC .... A61F 2002/30736; A61F 2002/3082; A61F 2002/30845; A61F 2002/4687; A61F 2/30942; A61F 2/4603; A61F 2/4657; A61F 2002/285
See application file for complete search history.

(56) References Cited

U.S. PATENT DOCUMENTS

2009/0087276 A1\* 4/2009 Rose .................... A61B 17/155
409/79
2010/0087824 A1 4/2010 Collazo
2010/0262150 A1 10/2010 Lian
2012/0239045 A1 9/2012 Li \* cited by examiner

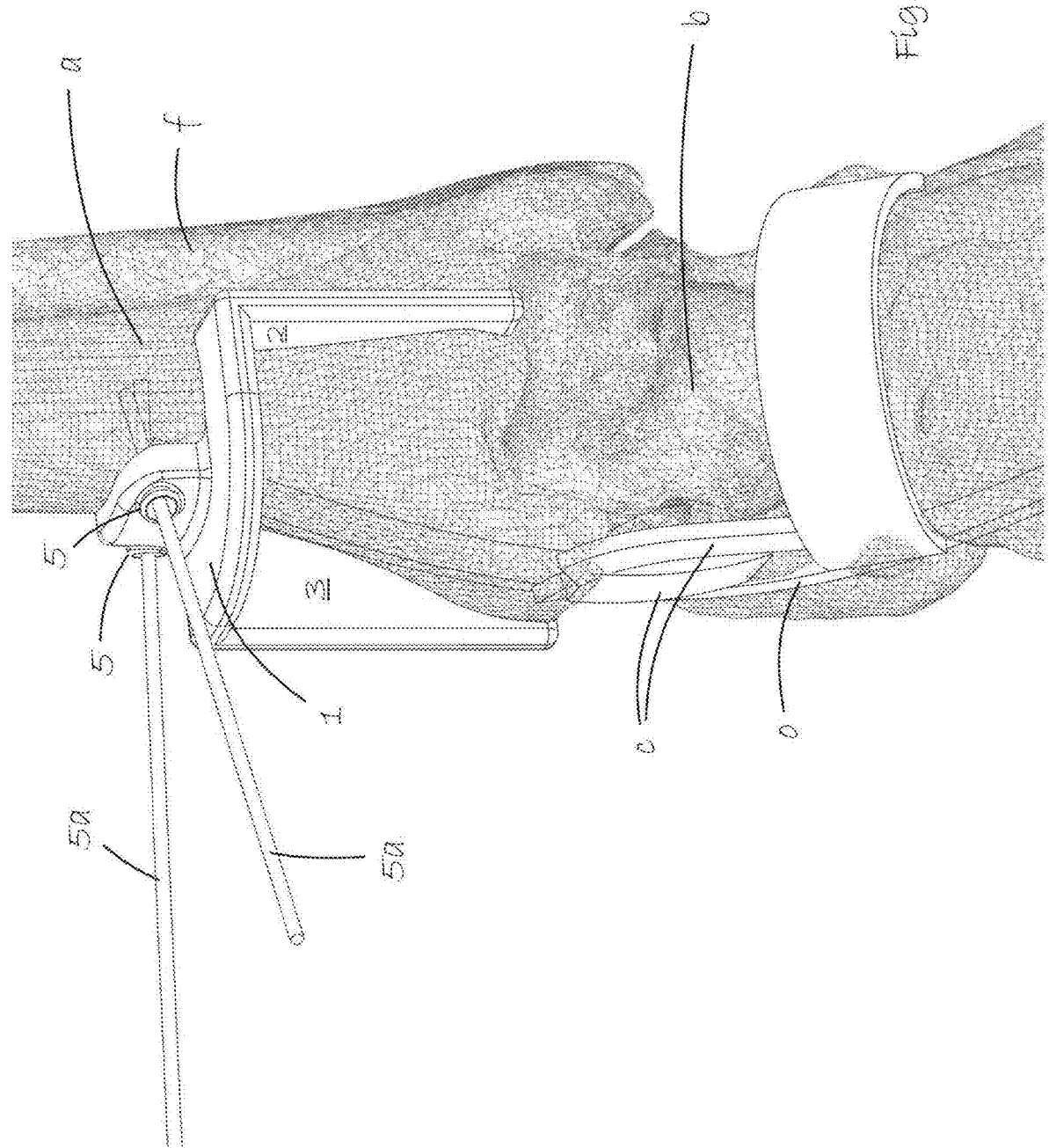

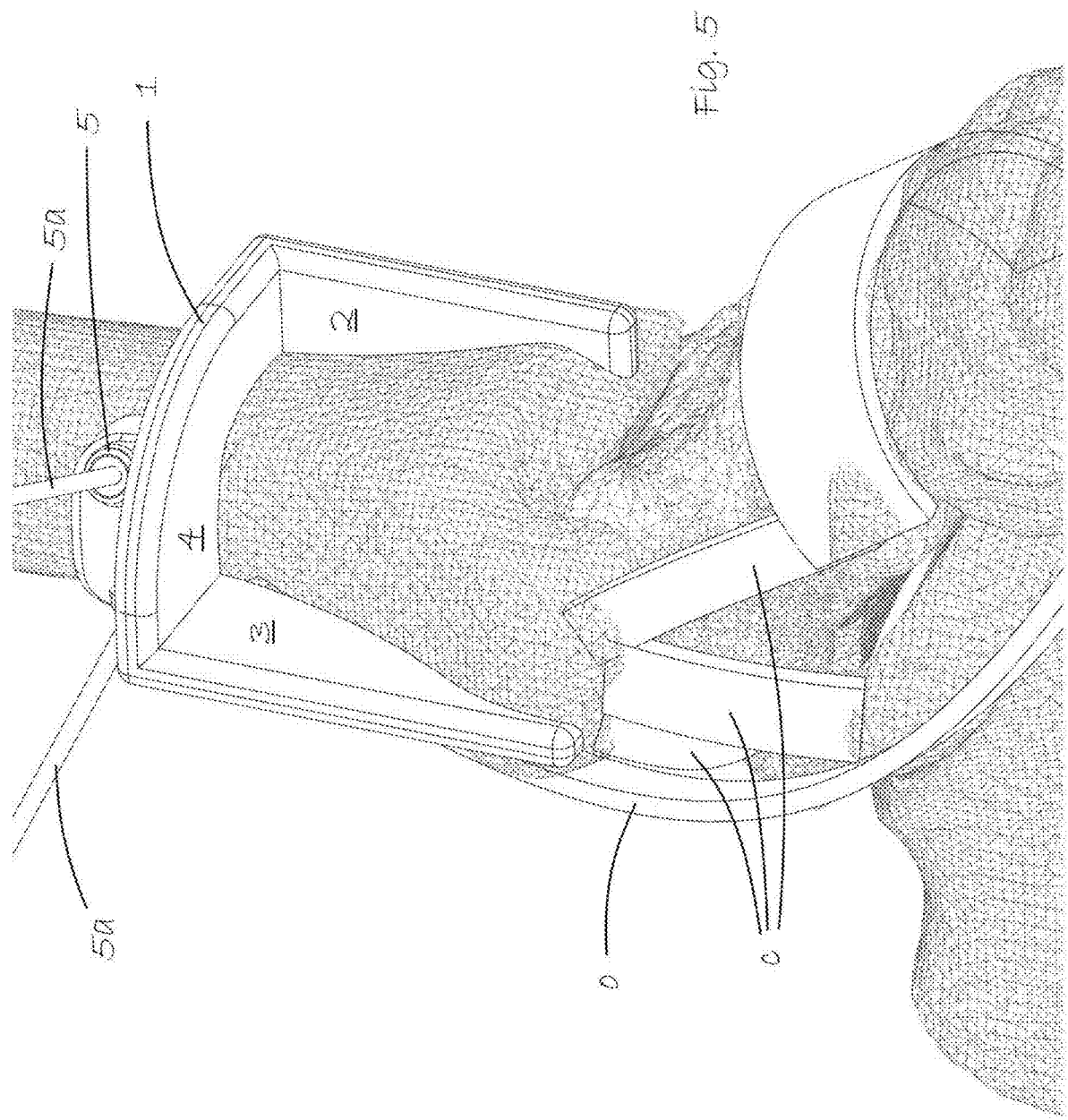

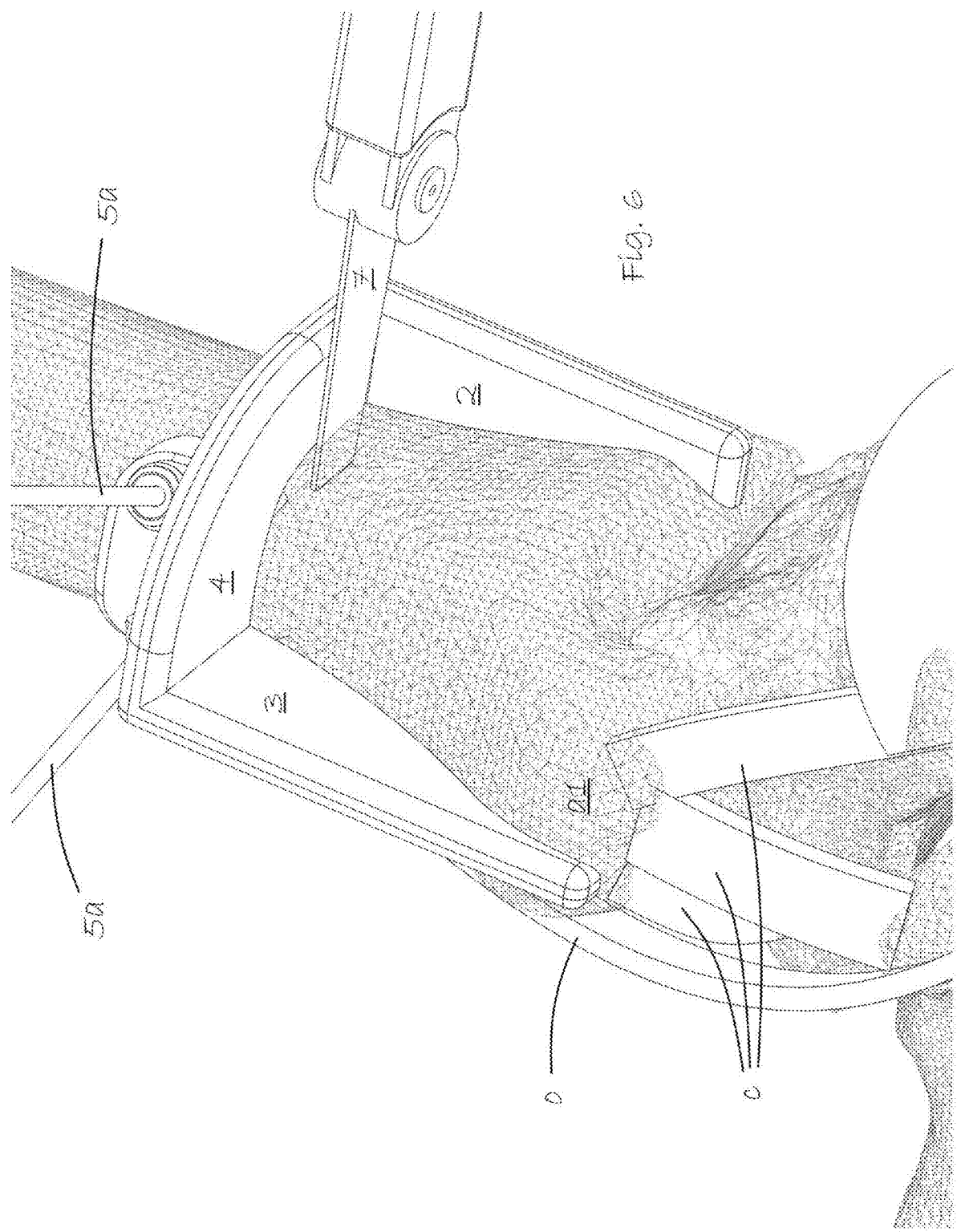

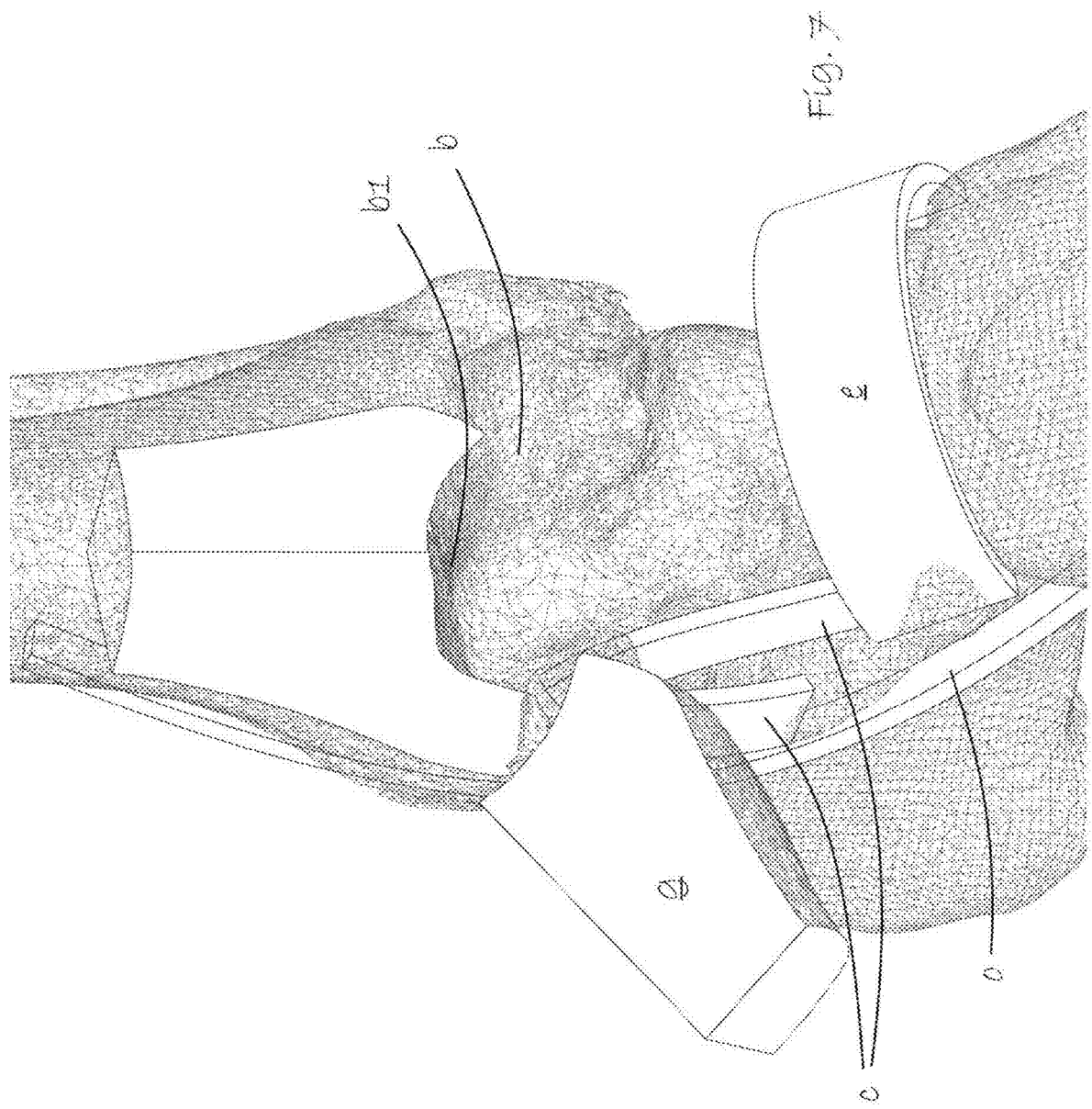

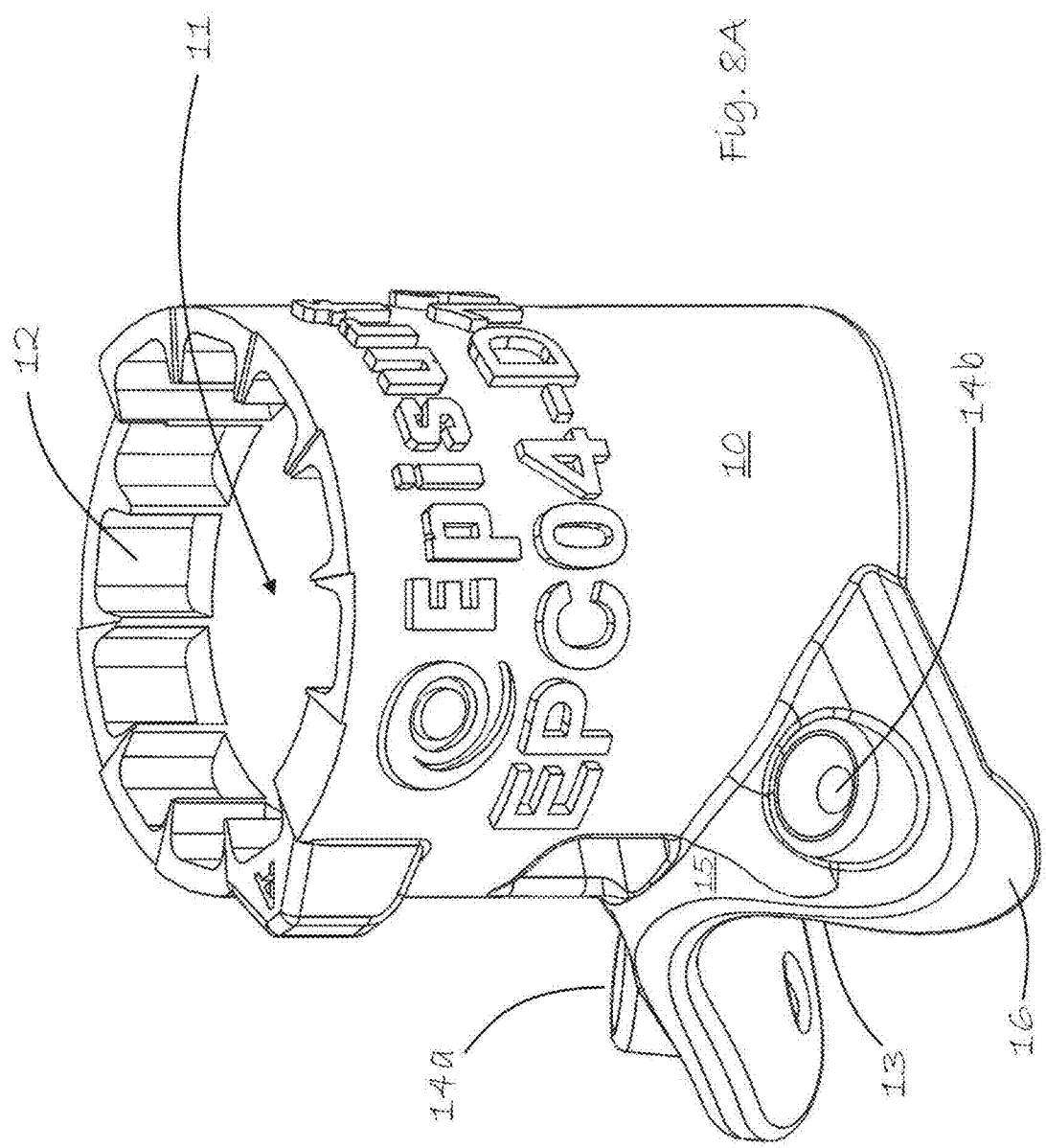

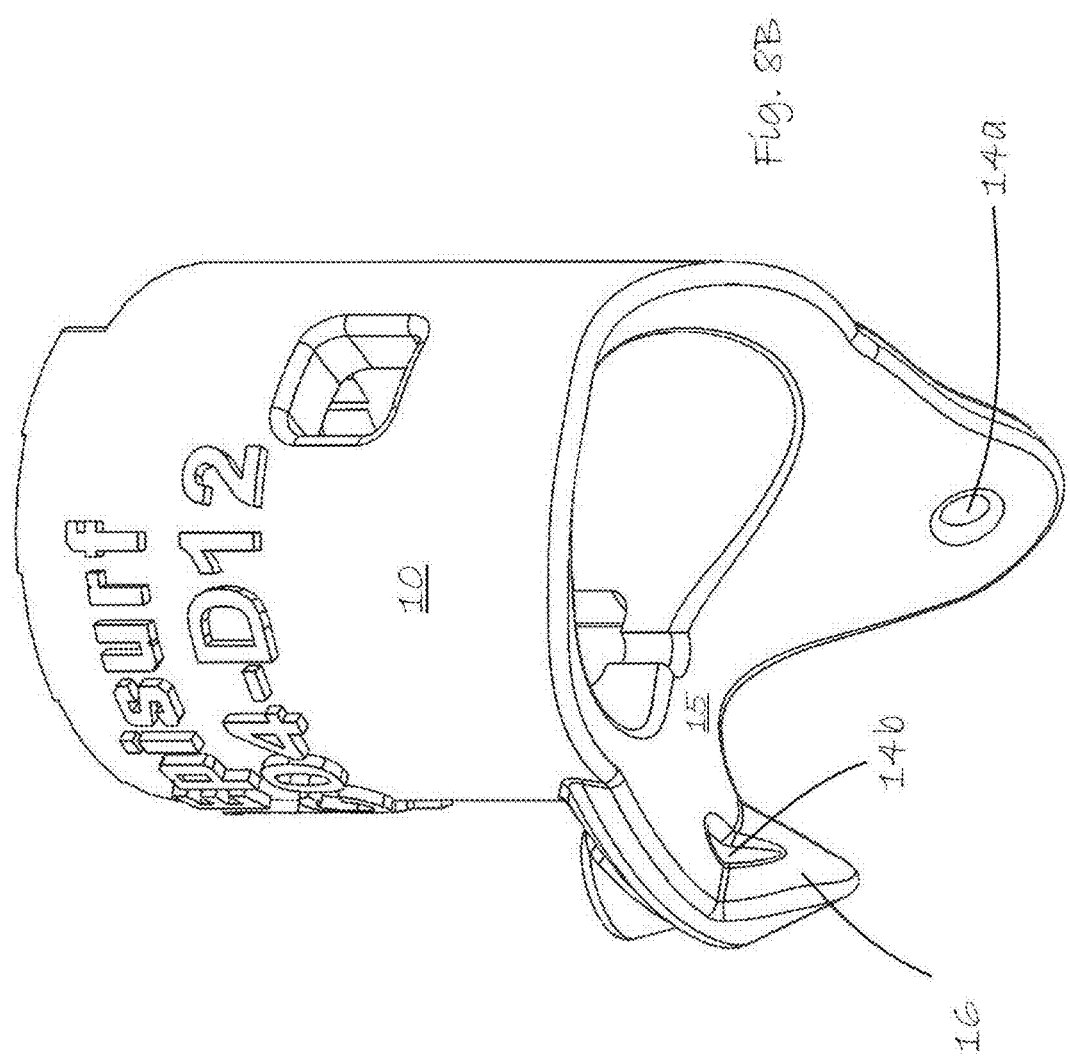

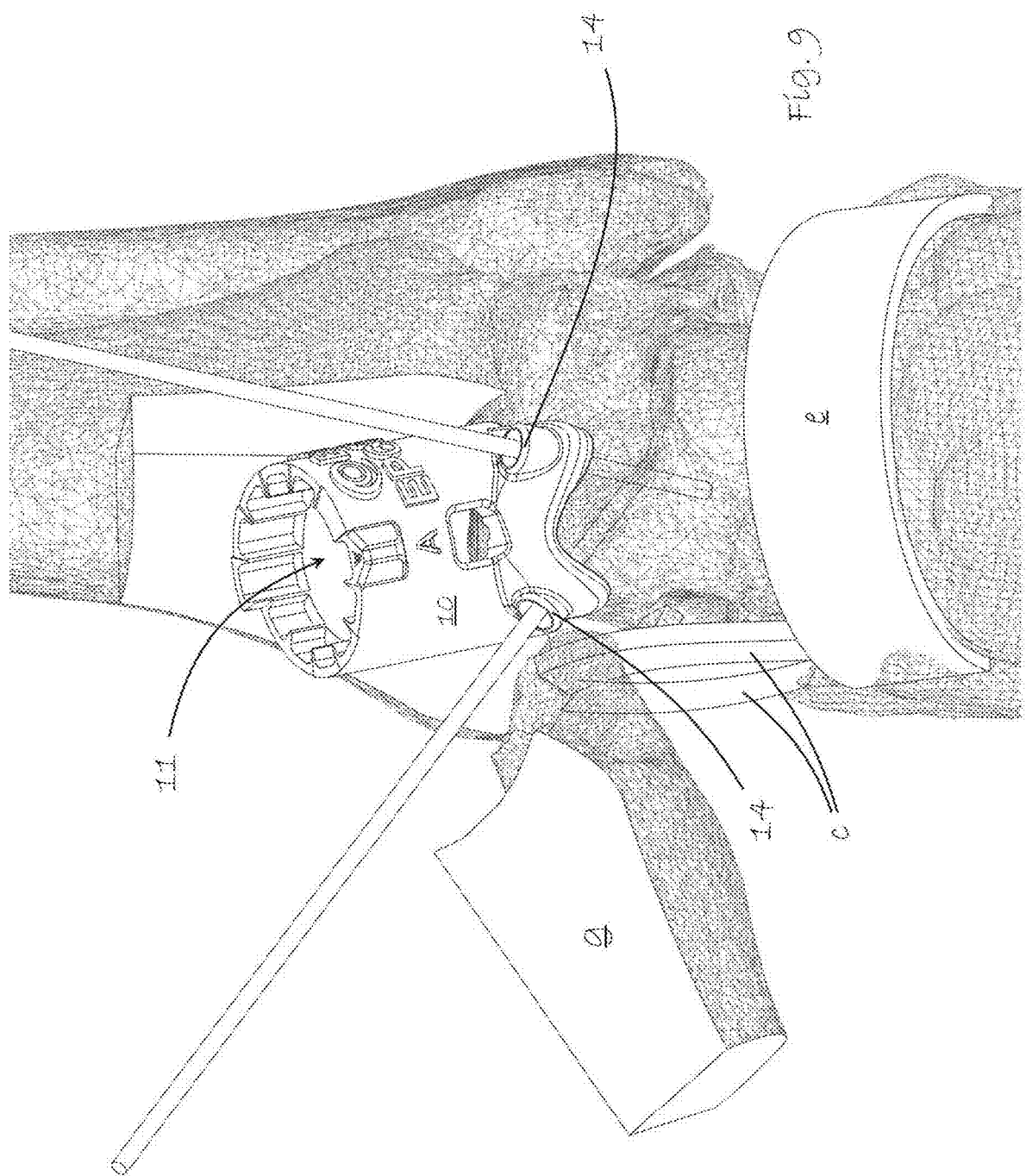

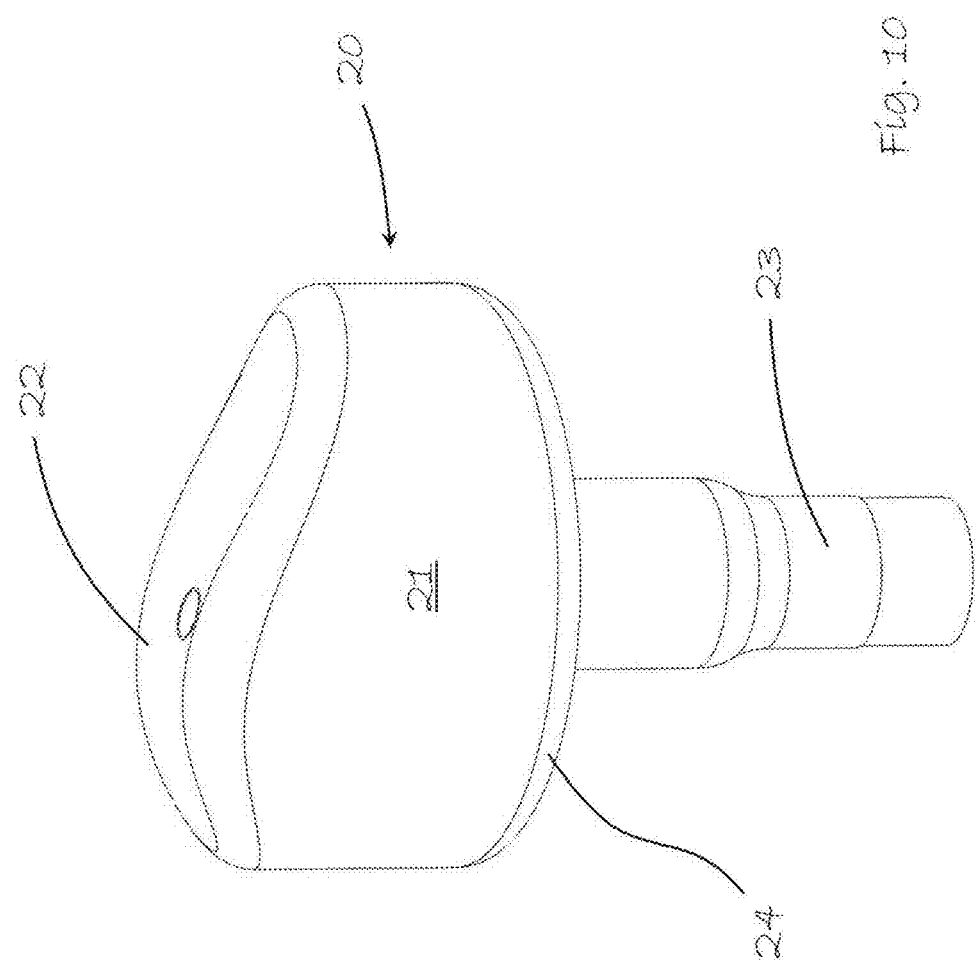

TOOLS FOR ASSISTING IN OSTEOTOMY PROCEDURES, AND METHODS FOR DESIGNING AND MANUFACTURING OSTEOTOMY TOOLS

CROSS-REFERENCE TO PRIOR APPLICATIONS

This application is a continuation-in-part application of U.S. patent application Ser. No. 15/526,539 filed May 12, 2017, which is a § 371 National Stage Application of PCT International Application No. PCT/EP2014/074533 filed Nov. 13, 2014, each of which are herein incorporated by reference in its entirety.

TECHNICAL FIELD

The present disclosure relates to a surgical kit, a saw guide and other related tools used in the osteotomy for temporary removal of a piece of the bone of a first bone structure to gain temporary access for treatment of defects of the cartilage and/or bone of a second bone structure, as well as methods for designing and manufacturing said tools.

BACKGROUND

Generally, the technology disclosed relates to surgical tools used in the temporary removal of a piece of a first bone structure to gain temporary access for surgical treatment of defects of a second bone structure. The defects of the second bone structure may e.g. be damage in the bone, cartilage or cartilage and underlying bone of the second bone structure.

In certain aspects, the technology disclosed relates to joint defects, such as osteochondral defects, of the talar dome which are mostly caused by a traumatic event. They may lead to deep ankle pain on weight bearing, prolonged swelling, diminished range of motion, and synovitis. The mean cartilage thickness of the talar dome is in the range 1.2 to 1.4 mm. Cartilage defects are strongly linked to damage in the subchondral bone. An important target in the treatment of talar osseochondral defects (OCDs) is repair of the subchondral bone. A healthy restored subchondral bone plate would decrease the pain, improve the load-bearing capacity of the ankle, and improve chondrocyte survival in the remaining cartilage.

Treatment options for talar osteochondral defects (OCDs) are numerous. High success rates have been reported for bone marrow stimulation techniques and osteochondral autograft transfer. Because osteochondral autograft transfer can cause knee morbidity at the donor site, debridement and bone marrow stimulation often remains the treatment of choice for primary OCDs, i.e., those without previous surgery, up to 15 mm in diameter. During debridement and bone marrow stimulation, the OCD is preferably approached by anterior ankle arthroscopy with the ankle in full plantar flexion for adequate exposure of the defect. However, the ankle is a congruent joint with limited surgical access. Some defects are located so far posteriorly that they may not be accessible by anterior ankle arthroscopy. During debridement and bone marrow stimulation, the OCD may for example be approached by anterior ankle arthroscopy with the ankle in full plantar flexion for adequate exposure of the defect. However, the ankle is a congruent joint with limited surgical access. Some defects are located so far posteriorly that they may not be accessible by anterior ankle arthroscopy.

If the lesion is located on the medial side of the talar dome (ca 60% of cases), most of these treatment options require an osteotomy, e.g. a medial malleolar osteotomy, to obtain sufficient access to the talar dome. There are different varieties of osteotomy to get access to the talar dome, but a medial malleolar osteotomy is an established approach for the operative treatment of medial osteochondral defects of the talar dome and fractures of the talar body.

Lesions after failed previous surgery or large lesions can be treated by various alternative surgical methods, including autologous cancellous bone grafting, osteochondral autograft transfer, osteochondral allograft transfer and autologous chondrocyte implantation (ACI) or treatment with resurfacing implants. These techniques are generally more complicated and require more bulky tools compared to debridement and bone marrow stimulation, thus requiring better access to the talar dome, especially for larger lesions. Disadvantages of these secondary methods include pain at the donor site, limited availability of graft material, and two surgical procedures in the case of ACI. An alternative without these disadvantages would be desirable. The methods mentioned above are sometimes combined with osteotomy for better access to the talar dome.

Because of the disadvantages of current secondary treatment methods, metal resurfacing inlay implants have been developed and started to reach the market. A precise surgical technique is required in terms of implantation depth, position, and orientation because of the biomechanical properties of the ankle joint. A protruding implant may damage the opposite cartilage by causing excessive contact pressures during loading, which is thought to be due to "plowing" of the cartilage. On the other hand, a deep implant might result in collapse of the adjacent cartilage due to insufficient support.

If the lesion is located on the medial side of the talar dome (ca 60% of cases), most of these treatment options require a medial malleolar osteotomy in order to obtain access to the talar dome. A medial malleolar osteotomy is an established approach for the operative treatment of medial osteochondral defects of the talar dome and fractures of the talar body. There are different varieties of osteotomy to get access to the talar dome. A commonly used osteotomy is the oblique medial malleolar osteotomy, which is a crucial step in the surgical implantation of the resurfacing inlay implants. To obtain a congruent joint surface after refixation, the osteotomy should be directed perpendicularly to the articular surface of the tibia at the intersection between the tibial plafond and medial malleolus. At an instructional course on the metallic implantation technique, surgeons experienced technical difficulties performing a successful medial malleolar osteotomy. The difficulties included sawing at an angle that allowed refixation of the distal fragment without creating an articular incongruence, as well as identifying the intersection between the tibial plafond and medial malleolus. Thus, knowledge of the angle of the osteotomy relative to an anatomic landmark such as the long tibial axis would be helpful for use during surgery, as well as surgical tricks to identify the intersection.

It has been reported that a medial malleolar osteotomy frequently led to local osteoarthritis and less favorable clinical findings than arthrotomy without osteotomy.

The advantages of implants over complete replacement of the joint have stimulated a further development of smaller implants that can be implanted with less invasive surgery. In this development there has also been an effort to achieve small joint implants, suitable for repair of a small bone and/or cartilage injury that have a minimal influence on the surrounding parts of the joint. In the current development, such small implants are designed with an implant body that may be formed as a mushroom cap with a hard surface to face the articulating side of the joint and a bone contacting surface engaging the bone below the damaged part of cartilage. The shape and the curvature of the articulating surface of the implant may be designed to be a reconstitution of the shape and the curvature of the part of the joint when it was undamaged. Such implants are usually designed as mushrooms with an implant body or head and with a peg or a rod projecting from the bone contacting side of the implant body for anchoring the implant into the bone. The cap of the mushroom for repair of the talus dome is often slanted or irregular to conform to the shape of the original undamaged ridge or dome of the talus.

There is a lack of talar metal resurfacing implants with an exact match of the undamaged talar anatomy, as well as metal resurfacing implants that can be placed not only at the edge of the medial talar dome, but placed more centrally on the medial talar dome.

Problems with the Prior Art

An osteotomy, which includes cutting out and temporarily removing a bone fragment of a first bone structure to gain access to a second bone structure for medical treatment of damage to the cartilage and/or bone of that second bone structure, can be a crucial step for any kind of treatment of various second bone structures. e.g. for the treatment with bone marrow stimulation, osteochondral grafting or the surgical implantation of resurfacing inlay implants into the second bone structure.

A commonly used osteotomy for the treatment of defects of the talar dome of the ankle joint is the oblique osteotomy, such as the medial malleolar osteotomy, which is a crucial step for obtaining access to the talar dome for treatment of the talus, e.g. the treatment with bone marrow stimulation, treatment through osteochondral grafting or the surgical implantation of resurfacing inlay implants. To obtain a congruent joint surface after refixation of the temporarily removed bone fragment, the osteotomy in state of the art solutions is often directed essentially perpendicularly to the articular surface of the tibia at the intersection between the tibial plafond and the medial malleolus. Failure to direct the osteotomy properly may lead to limited exposure of the defect site (too medial), or violate the weight-bearing cartilage on the tibial plafond (too lateral).

Implants having a top cap surface customized to each patient to replicate the surface of the talus dome before it was injured, must be implanted so that the forces, applied during standing and walking via the lower condylar surfaces of the tibia against the new implant will act axially in relation to the implantation peg, for optimum force absorption and length of life. The anatomy of the talocrural area differs from that of the knee in that it is very difficult for the surgeon to access the dome of the talus. It is covered by the lower condylar surface of the tibia, as well as being encased by a many different muscles, tendons and ligaments extending between the tibia and the calcaneus, the navicular and the talus, particular the medial (deltoid) ligaments and flexor digitorum longus and the tibialis posterior muscles. Any severing of these muscles and tendons to gain access to the talus dome will create exceptional and sometimes permanent problems as regards repair and rehabilitation.

In this osteotomy procedure aimed at gaining access to the treatment area, e.g. the dome of the talus, a drilling, or predrilling, through the saw cutting plane of the piece of the tibia to be removed to create fixation holes in the inner portions of the tibia may be performed. The drilling, or pre-drilling, of the fixation holes is preferably performed before the saw cutting and the created fixation holes through the malleolus and into the inner portions of the tibia are later used for refixation of the temporarily removed bone fragment. In this connection, there is a need for an improved osteotomy procedure including a faster and more precise and reliable pre-drilling and refixation procedure which would first of all increase the likelihood of a congruent joint surface after refixation but also increase the likelihood of preserving the deltoid ligament that originates more distally, yet reducing the risk for a drilling that can cause severing of any muscles, tendons and ligaments, or a screw placement causing disruption of the deltoid ligament. Any significant improvement to the osteotomy procedure, including a faster and more precise and reliable pre-drilling and refixation, would be almost impossible to achieve with the currently used methods and tools for free-hand drilling of the fixation holes, or with an osteotomy where the saw cutting procedure and the pre-drilling and refixation procedure are essentially separate procedures which are not strongly linked to each other.

If a bone fragment in form of a piece of the lower tibia, or malleolus, is sawn out to gain access to the talus dome, it is necessary that the bone be sawn precisely on the first try, so that the bone fragment, or bone segment, will fit precisely in place when put back and screwed in place. For better healing and alignment, the single saw cut is preferably a partial cut, not a through cut. The last part of the bone fragment is generally loosened with aid of a surgical tool referred to as osteotome, tapped down to create breakage of the last part of bone. It is also important that the drilling, or predrilling, of the fixation holes is performed in a precise and reliable manner.

It is thus necessary to expose the talus dome by cutting out a corner of the lower medial tibia, under a number of difficult constrictions:

avoiding all important tendons, muscles and ligaments and leaving them attached and intact,
avoiding the anterior tibial artery,
providing enough exposed space to correctly perform a surgical treatment of at least one of a bone and a cartilage damage of the talus dome, and correctly drill for and drive in the implant at the correct angle,
making the drilling of the fixation holes and the sawing of the bone cut precise and correct on the first try,
facilitating a correct refixation of the temporarily removed bone fragment in form of a piece of the lower tibia, e.g. a piece of the malleolus, in its correct position for healing and for creating a congruent joint surface,
avoiding cutting through the bone fragment and into the cartilage of the talar dome, damaging the articular surface.

A kit according to the disclosure makes this possible in a precise and reproducible manner, providing for an operation which would be almost impossible to achieve with free-hand cutting, and placement of the implant.

SUMMARY

The entire complex of problems listed above finds its solution in the invention as defined in the appended patent claims.

The technology disclosed can generally be applied for any osteotomy followed by fixation of an anatomical part or a device. In some embodiments, the technology can be applied for temporary osteotomy of a part of the distal tibia for access to the medial talar dome of the ankle joint. In other embodiments, the technology can be applied for access to the lateral part of the talus through osteotomy of the lateral part of the distal tibia, or osteotomy of the fibula. In example embodiments, the joint can be a wrist where osteotomy of radius is performed. In yet other embodiments, the joint can be an elbow where an olecranon osteotomy is performed for access to humerus.

The inventors have identified a need for an improved osteotomy procedure including a faster and more precise and reliable pre-drilling and refixation procedure which would first of all increase the likelihood of a congruent joint surface after refixation but also increase the likelihood of preserving the deltoid ligament that originates more distally, yet reducing the risk for a drilling that can cause severing of any muscles, tendons and ligaments, or a screw placement causing disruption of the deltoid ligament. Thus, it is important that the drilling, or predrilling, of the fixation holes is performed in a precise and reliable manner.

Generally, the technology disclosed proposes a surgical saw guide, and a method for designing a surgical saw guide suitable for use in osteotomy and the temporary osteotomic removal of a bone fragment of a first bone structure of a patient for exposing a second bone structure for surgical treatment. The saw guide may comprise a slit, or opening, configured to receive a saw cutting tool and to guide the saw cutting tool to form a single saw cut in a straight direction at an angle to an inner engagement surface of the saw guide. The inner engagement surface of the saw guide may be adapted to at least partly conform to the surface of the first bone structure of a patient. The saw guide may further comprise, as an integral part, a drill guide having at least one hole with a certain diameter, thickness or depth, orientation and position on the saw guide to thereby be configured to guide the drilling, or pre-drilling, of a hole in a straight direction at an angle relative to the saw cutting direction provided by the guidance of the slit, or opening.

The slit, or opening, and the portion of the saw guide comprising said slit, may be configured to be used to form a single saw cut in the removal of a bone fragment of a first bone structure to gain access to a second bone structure for medical treatment of damage to the cartilage and/or bone of that second bone structure. The portion of the saw guide comprising said slit, or opening, may be designed and configured with a height that matches, or corresponds to, the length of the sawblade to be used during sawing to thereby make the power tool used during sawing stop against the top surface of the portion of the saw guide, thereby minimizing the risk of unintentionally sawing too far. In certain example embodiment of and method for designing the saw guide, the dimensions, e.g. the height, of the portion of the saw guide may be customized, e.g. via imagery of the patient's bone structure through e.g. MRI, CT or X-ray and/or based on the sawblade selected. As an example, the length of the sawblade and/or the thickness of the malleolus of a specific patient may be used to determine the height of the portion of the saw guide.

The at least one hole of the drill guide of the above saw guide may be configured to guide the drilling, or pre-drilling, of at least one hole past the single saw cutting plane provided by the guidance of said slit and into the inner portions of the first bone structure there behind, thereby being adapted to provide for the pre-drilling of at least one fixation hole through the bone fragment to be removed, past the saw cutting plane and into the inner portions of the first bone structure that can be used for facilitating correct refixation of the removed bone fragment in its original, or substantially original, position after performed treatment, e.g. surgical treatment, by the use of fixation means, e.g. in the form of at least one screw. The use of the word substantially in substantially original position relates to that a small portion of the first bone structure is pulverized in the saw cutting procedure which, in turn, implies that the bone fragment, when remounted, is fixed to the inner portions of the first bone structure in a position which deviates slightly from its original position. The fixation means are inserted into the first bone structure through the pre-drilled at least one fixation hole, thereby fixing the temporarily removed bone fragment to the first bone structure.

In non-limiting embodiments of the technology disclosed, a plurality of screws are used as fixation means for the refixation of the removed bone fragment in its original, or substantially original, position after performed treatment. The plurality of screws are screwed into the first bone structure through a plurality of fixation holes created by the pre-drilling, thereby fixing the temporarily removed bone fragment to the first bone structure. In alternative embodiments, the fixation means used for the refixation of the removed bone fragment may be a plurality of nails, which are driven into the first bone structure through a plurality of fixation holes, thereby fixing the temporarily removed bone fragment to the first bone structure. In yet other alternative embodiments, the fixation means used for the refixation of the removed bone fragment may be a plurality of fixation pins, e.g. self-tapping threaded pins, which are driven into the first bone structure through a plurality of fixation holes, thereby fixing the temporarily removed bone fragment to the first bone structure.

According to certain aspects of the technology disclosed, the surgical saw guide is suitable for use in oblique osteotomy and the temporary osteotomic removal of a bone fragment of a tibia for exposing the talus dome for surgical treatment. The saw guide may comprise at least one first opening, or pin hole, adapted to receive a fixation means, such as a pin, where the at least one hole has an orientation adapted to guide the temporary fixation of the saw guide to the tibia. The saw guide may comprise a slit, or opening, configured to receive a saw cutting tool and to guide the saw cutting tool to form a single saw cut in a straight direction at an angle to an inner engagement surface of the saw guide. The inner engagement surface of the saw guide may be adapted to at least partly conform to the distal or lower portion of the tibia of a patient. The saw guide may further comprise, as an integral part, a drill guide having at least one hole having a certain diameter, thickness/depth, orientation and position on the saw guide to thereby be configured to guide the drilling of a hole in a straight direction and at a certain angle relative to the saw cutting direction provided by the guidance of the slit, or opening. The at least one hole of the drill guide may also be designed to have a certain diameter adapted to be suitable for a certain type of drill having certain dimensions, including a certain diameter, so as to achieve a fit upon insertion of the drill into the at least one hole for optimal drilling, or pre-drilling, of the fixation holes into the tibia.

The slit, or opening, and the portion of the saw guide comprising said slit, may be configured to be used to form a single saw cut in the removal of a bone fragment of the tibia to gain access to the medial talar dome of the ankle joint for a specific treatment of damage to the cartilage and/or bone of the talus. The at least one hole of the drill guide of the above saw guide may be configured to guide the drilling, or pre-drilling, of at least one hole through the bone fragment, or piece of the tibia, to be removed, past the single saw cutting plane provided by the guidance of said slit and into the inner portions of the tibia there behind, thereby being adapted to provide for the pre-drilling of at least one fixation hole which can be used for facilitating correct refixation of the removed bone fragment in its original position, or substantially original, after performed treatment, e.g. surgical treatment, by the use of fixation means, e.g. in the form of at least one screw. The fixation means are inserted through the bone fragment to be removed and into the inner portions of the tibia through the pre-drilled of at least one fixation hole fixation, thereby fixing the temporarily removed bone fragment to the inner portions of the tibia. The use of the word substantially in substantially original position relates to that a small portion of the tibia is pulverized in the saw cutting procedure which, in turn, implies that the bone fragment, when remounted, is fixed to the inner portions of the tibia in a position which deviates slightly from its original position. In example embodiments, the portion of the saw guide comprising said slit, or opening, may be designed and configured with a height that matches, or corresponds to, the length of the sawblade to be used during sawing to thereby make the powertool used during sawing stop against the top surface of the portion of the saw guide, thereby minimizing the risk of unintentionally sawing too far, e.g. into the articular surface of the talus. In certain example embodiment of a method for designing the saw guide, the dimensions, e.g. the height, of the portion of the saw guide may be customized, e.g. via imagery of the patient's bone structure through e.g. MRI, CT or X-ray and/or based on the sawblade selected. As an example, the length of the sawblade to be used and/or the thickness of the malleolus of a specific patient may be used to determine the height of the portion of the saw guide.

In non-limiting embodiments of the technology disclosed, a plurality of screws are used as fixation means for the refixation of the removed bone fragment in its original, or substantially original, position after performed treatment. The plurality of screws are then screwed into the tibia through a plurality of fixation holes created by the pre-drilling, thereby fixing the temporarily removed bone fragment to the tibia. In alternative embodiments, the fixation means used for the refixation of the removed bone fragment to the inner portions of the tibia may be a plurality of nails, which are driven through the bone fragment into a plurality of fixation holes created in the inner portions of the tibia, where the fixation holes are created by the pre-drilling, thereby fixing the temporarily removed bone fragment to the tibia. In alternative embodiments, the fixation means used for the refixation of the removed bone fragment may be a plurality of fixation pins, e.g. self-tapping threaded pins, which are driven into the tibia through a plurality of fixation holes, thereby fixing the temporarily removed bone fragment to the tibia.

In certain embodiments of the technology disclosed, the at least one hole of the drill guide has a certain orientation and position on the saw guide to thereby be configured to guide the drilling, or pre-drilling, of at least one hole past the single saw cutting plane provided by the guidance of said slit and into the inner portions of the tibia bone there behind, thereby being adapted to provide for the pre-drilling of at least one fixation hole in the inner portions of the tibia bone that can be used for facilitating correct refixation of the removed bone fragment in its original, or substantially original, position after performed surgical treatment, e.g. by the use of fixation means in the form of at least one screw.

In certain embodiments, the at least one hole of the drill guide is configured to guide the drilling along a straight line at a specific angle direction with respect to at least one of:
 at least a portion of the inner engagement surface adapted to conform to the distal or lower portion of the tibia of a patient,
 the longitudinal axis of the patient, and
 the direction for forming said single saw cut.

According to certain embodiments, the at least one hole of said drill guide is configured to guide the drilling in a direction at an angle or within an angle range to the longitudinal tibial axis of a patient, wherein said angle or angle range is within the angle range of 50-70 degrees to the longitudinal tibial axis of a patient.

According to certain embodiments, the at least one hole of said drill guide is configured to guide the drilling in a direction along a straight line at an angle 3 at 60 degrees, or close to 60 degrees, to the longitudinal tibial axis of a patient.

According to certain embodiments, the at least one hole of the drill guide is configured to guide drilling in a direction at an angle or within an angle range to the direction for forming said single saw cut, wherein said angle or angle range is within the angle range of 80-100 degrees to the direction for forming said single saw cut.

According to certain embodiments, the at least one hole of the drill guide is configured to guide drilling in a perpendicular direction, or close to 90 degrees, with respect to the direction for forming said single saw cut.

According to certain embodiments, the slit, or opening, for guiding a saw cutting tool is configured to guide a saw cutting tool to form a single saw cut at an angle or within an angle range to the longitudinal tibial axis of a patient, wherein said angle or angle range is within the angle range of 15-50 degrees to the longitudinal tibial axis of a patient.

According to certain embodiments, the slit, or opening, for guiding a saw cutting tool is configured to guide a saw cutting tool to form a single saw cut in a direction at a 30 degrees angle, or close to 30 degrees, to the longitudinal tibial axis of a patient.

In certain example embodiments, the saw guide further comprises an opening forming an inspection window adapted to allow visual inspection of how well the saw guide conforms to the distal or lower portion of the tibia of a patient, thereby facilitating adjustment of the positioning of the saw guide to provide for a correct positioning of the saw guide to the distal or lower portion of the tibia of the patient, to provide for both a more precise saw cutting procedure and a more precise drilling procedure.

The technology disclosed further provides a surgical kit including the saw guide according to any of the embodiments described above. In certain aspects, the surgical kit includes fixation means in form of e.g. screws such as e.g. titanium screws, which have dimensions and a certain length configured to allow for a correct refixation of the temporarily removed bone fragment, e.g. the fixation means have a length corresponding to, or adapted to, the depth of the holes pre-drilled through the bone fragment and beyond the saw cutting plane into the inner portions of the tibia.

In other example embodiments, the surgical kit of the present disclosure may include a verification tool, or depth meter tool, having a depth stop designed to be engaging a powertool, used for the saw cutting procedure, at a specific depth, to prevent insertion of saw cutting blades into the slit of the saw guide that cut beyond a certain length. In the verification process, the saw attachment and sawblade are first attached to the powertool and the depth meter is used for verifying that the selected sawblade has the correct dimension for a designed saw guide.

In other embodiments related to the example use of the technology disclosed in the surgical treatment by the implantation of an implant into a second bone structure, e.g. by resurfacing of an implant into the dome of the talus, the surgical kit of the present disclosure may include a hollow tubular shell suitable for guiding correct preparations such as implant pre-drilling at the surgical site of the talus dome. In these embodiments, the surgical kit of the present disclosure may also include different sockets adapted to be positioned in the hollow tubular shell. One such socket is a pin socket configured with a steering hole in the form of a through hole. The pin socket, when positioned in said hollow tubular shell, provides mechanical support and directional guidance for vertical drilling through said steering hole and into the articular surface of the second bone structure, creating a steering hole for further drilling to remove cartilage and bone to prepare the site for implantation of an implant. In some embodiments, the pin socket, when positioned in said hollow tubular shell, may provide mechanical support and the directional guidance for vertical drilling through the steering hole of the pin socket and into the articular surface of a joint to form a steering hole in the articular surface of a joint for further drilling to remove cartilage and bone to prepare the site for implantation of an implant. In example embodiments, the pin socket, when positioned in said hollow tubular shell, provides mechanical support and directional guidance for vertical drilling through said steering hole and into the dome of the talus, creating a steering hole for further drilling to remove cartilage and bone to prepare the site for implantation of an implant into the dome of the talus. Two other sockets; a drilling socket and an adjustment socket, may further be used in the process of removing a portion of the talus bone for creating a recess for the implant, preceding hammering of the surgical implant into place in the talus dome. When the pre-drilling through the steering hole of the pin socket has been performed, the drilling socket is mounted into the hollow tubular shell and the drilling operation continues until the drill stops at the top of the drilling socket. The drilling guide is removed and the adjustment socket is instead inserted into the hollow tubular shell. When inserting the drill into the adjustment socket, the drill is inserted into the pre-drilled hole. Preferably, the drill body should not be in contact with the cartilage surface when the drilling starts. The drilling into the talar dome continues until the drill stops at the top of the adjustment socket. A flushing device and suction may be used to cleanse the drilled hole. For the final placement of the implant into the drilled hole, a mandrel and/or a hammer may be used to gently tap down the surgical implant into the bone until bottomed.

In certain example embodiments, the surgical kit may, in addition to the various embodiment of a saw guide described in this disclosure, also include at least one of a surgical implant, a dummy implant, a drill, a mandrel and a hollow tubular shell used for drilling of the damaged area on the articular surface of a second bone structure in the surgical procedure of implantation of resurfacing inlay implants.

The technology disclosed further proposes a method for designing a saw guide comprising the above-mentioned technical features. The method for designing the saw guide includes the designing of a saw guide which comprises as integral parts both a slit configured to guide the saw cutting in a first direction and a drill guide having at least one hole configured to guide the pre-drilling in a second direction different from the first direction.

In certain embodiments, the technology disclosed proposes a method for designing any of the above-mentioned embodiments of a saw guide which includes a step for designing the at least portion of the surface of the inner engagement surface adapted to conform to the distal or lower portion of the tibia of a patient to be individually patient customized on the basis of radiologically obtained patient data, such as MR, CT or X-ray imaging.

In certain embodiments, the technology disclosed proposes a method for designing any of the above-mentioned embodiments of a saw guide which includes a step for designing the placement and orientation of the at least one hole of the drill guide to be individually patient customized on the basis of radiologically obtained patient data, such as MR, CT or X-ray imaging.

In certain embodiments, the technology disclosed proposes a method for designing any of the above-mentioned embodiments of a saw guide which includes a step for designing the placement and orientation of the slit, or opening, to be individually patient customized on the basis of radiologically obtained patient data, such as MR, CT or X-ray imaging.

In other embodiments, the technology disclosed proposes a method for designing any of the above-mentioned embodiments of a saw guide which includes a step for designing the at least one hole of the drill guide, said at least one hole having a certain orientation and position on the saw guide, to be individually patient customized on the basis of radiologically obtained patient data, such as MR, CT or X-ray imaging, in that the drilling direction provided by the position and orientation of the at least one hole is designed to have a patient customized angle relationship to at least one of the distal or lower portion of the tibia of a patient and the longitudinal axis of the patient.

In yet other embodiments, the technology disclosed proposes a method for designing any of the above-mentioned embodiments of a saw guide which includes a step for designing the slit, or opening, to be individually patient customized on the basis of radiologically obtained patient data, such as MR, CT or X-ray imaging, in that the saw cutting direction, and thereby also the saw cutting plane, provided by the position and orientation of said slit is designed to have a patient customized angle relationship to at least one of the distal or lower portion of the tibia of a patient and the longitudinal axis of the patient.

In yet other embodiments, the technology disclosed proposes a method for designing any of the above-mentioned embodiments of a saw guide which includes at least one step for designing both the saw cutting direction provided by the position and orientation of said slit, or opening, and the drilling direction provided by position and orientation of the at least one hole of the drill guide to have a patient customized angular relationship to at least one of the distal or lower portion of the tibia of a patient and the longitudinal axis of the patient.

Thus, the above-mentioned saw guide comprises as integral parts both a slit configured to guide the saw cutting in a first direction and a drill guide having at least one hole configured to guide the predrilling in a second direction different from the first direction. The technology disclosed enables the design of a saw guide comprising at least one hole of a drill guide having a fixed physical relationship to a slit suitable to be used for saw cutting, i.e. both a positional and angular relationship between the at least one holes of the drill guide and the saw cutting slit, thereby enabling the design of a saw guide having a fixed angular relationship between the angle direction of the saw cutting provided by the guidance direction of the slit and the angle direction for predrilling of the at least one fixation hole provided by the guidance direction of the at least one hole of the drill guide. In certain embodiments of the technology disclosed, this fixed angular relationship (between the guidance direction for the saw cutting direction provided by the orientation of the slit and the guidance direction of the predrilling of the at least one fixation hole provided by the at least one hole of the drill guide of the at least one fixation hole) is individually patient customized on the basis of radiologically obtained patient data, such as MR, CT or X-ray imaging. The thickness, or depth, of the slit and the dimensions and/or shape of the slit area of the slit, i.e. the longitudinal length and width of the slit area, may also be designed to be adapted and optimized to the length, width, and/or shape of a certain type of sawblade selected for the saw cutting procedure. The dimensions and/or depth/height of the portion of the saw guide which comprises the slit may be customized based on the sawblade selected.

In certain embodiments, the osteotomy and the surgical tools used, e.g. the design of the saw guide, can be adapted to the selected treatment of the damage, e.g. the damaged portions of a talus. The design of the saw guide may be based on both radiologically obtained patient data, such as MR, CT or X-ray imaging, and at least one of the selected type of treatment of the damaged area and, optionally, the size and location of the osteotomy. As an example, a drill guide, e.g. in form of a hollow tubular shell used for the implantation of a surgical implant, which has larger dimensions or a larger diameter, may require more space which in turn may require a larger osteotomy and the use of a saw guide that is designed for a larger osteotomy. A hollow tubular shell is designed to cover with its hollow part the damaged area of the talus to be repaired and is used for supporting the drilling on the talus dome, providing for a bore which is used for insertion of a surgical implant into the talus.

In certain embodiments, the technology disclosed may generally provide for patient-specific surgical kits including patient-specific saw guides and associated tools and components for use in osteotomy, low tibial or medial malleolar osteotomy, for example. The patient-specific saw guides can be used either with conventional or patient-specific implant components prepared with computer-assisted image methods. Computer modeling for obtaining three dimensional images of the patient's anatomy using MRI or CT scans of the patient's anatomy, and the patient-specific guides and templates can be provided by various CAD programs and/or software available.

In example embodiments, the patient-specific saw guides and associated patient-specific openings, holes and/or slits disclosed herein can be generally formed using computer modelling based on the patient's three-dimensional anatomic image generated from image scans. In specific embodiments, the design of the patient-specific saw guide and associated patient-specific openings, holes and/or slits disclosed herein may also be determined partly based on the patients three-dimensional anatomic image generated from image scans and partly on other requests, e.g. concerning the size and location of the osteotomy, which may be requested by the surgeon performing the osteotomy.

The patient-specific saw guides can have a three-dimensional inner engagement surface that is made to at least partly conformingly contact and match a three-dimensional image of the patient's bone surface, by the computer methods discussed above. In certain aspects of the technology disclosed, the patient-specific saw guide may also include customized guiding formations, such as a patient-customized drill guide and/or a patient-customized slit, or opening.

In various embodiments, the patient-specific saw guide comprises a slit, e.g. a patient-specific slit, for receiving and guiding a cutting blade at certain cutting plane orientations, e.g. relative to a selected anatomic axis for the specific patient. The patient-specific saw guide can also include drill guide formations and at least one hole for guiding the drilling, or predrilling, associated with the osteotomy procedure, at specific drilling orientations, e.g. relative to a selected anatomic axis of a specific patient. The geometry, shape and orientation of the various features of the patient-specific saw guide, as well as various patient-specific implants and other patient-specific tools that optionally may be used together with the saw guide according to certain example embodiments of the technology disclosed, can be determined during the pre-operative planning stage of the procedure in connection with the computer-assisted modelling of the patients anatomy.

In example embodiments of the technology disclosed, the saw guide may be individually made specific to the patient's specific anatomy and to the specific damage to the second bone structure, possibly through the following saw guide design steps:

a. identifying a damage of a second bone structure through radiological images such as MR, CT or X-ray images or through arthroscopy;
b. planning the size and the location of an osteotomy needed to get access to the second bone structure to perform a specific treatment of the damage;
c. creating a virtual 3D model of at least one of a first and the second bone structure from radiological images such as MR, CT or X-ray images; and
d. virtually designing a patient specific osteotomy guide based on the 3D model of at least one of the first and second bone structure and the size and location of the osteotomy needed.

In various embodiments, the surgical saw guide may be manufactured by a 3D printing process in which material is joined or solidified under computer control to create the surgical saw guide. The method of manufacturing by a 3D printing process may include building the surgical saw guide from computer-aided design (CAD) data by successively adding material layer by layer. The CAD data may further be based on a virtually designed patient specific osteotomy saw guide based on the 3D model of the at least portion of the first bone structure and the size and location of the osteotomy needed.

According to example embodiment, the above method of manufacturing the saw guide in a 3D printing process may be preceded by the following steps of virtually designing a patient specific osteotomy saw guide:

a. identifying at least one of a bone and a cartilage damage of the second bone structure through radiological images such as MR, CT or X-ray images;
b. planning the size and the location of an osteotomy needed to get access to the second bone structure in the surgical treatment of said at least one of a bone and cartilage damage of the second bone structure;
c. creating a 3D model of at least portions of at least one of a first bone structure and the second bone structure from radiological images such as MR, CT or X-ray images; and
d. virtually designing a patient specific osteotomy saw guide based on the 3D model and the size and location of the osteotomy needed.

In various embodiments, a surgical saw guide configured to be used for an osteotomy of a part of distal tibia for access to the medial talar dome of the ankle joint is manufactured by a 3D printing process in which material is joined or solidified under computer control to create the surgical saw guide. The method of manufacturing of the saw guide for an osteotomy of a part of distal tibia by a 3D printing process may include building the surgical saw guide from computer-aided design (CAD) data by successively adding material layer by layer. The CAD data may further be based on a virtually designed patient specific osteotomy saw guide based on the 3D model of the at least portion of the first bone structure and the size and location of the osteotomy needed.

According to example embodiment, the above method of manufacturing a saw guide suitable for an osteotomy of a part of distal tibia in a 3D printing process may be preceded by the following steps of virtually designing a patient specific osteotomy saw guide:
 a. identifying at least one of a bone and a cartilage damage of the talus through radiological images such as MR, CT or X-ray images;
 b. planning the size and the location of an osteotomy needed to get access to the dome of the talus in the treatment, e.g. surgical treatment, of said at least one of a bone and cartilage damage of the talus;
 c. creating a 3D model of at least portions of at least one of the tibia and talus from radiological images such as MR, CT or X-ray images; and
 d. virtually designing a patient specific osteotomy saw guide based on the 3D model and/or the size and location of the osteotomy needed.

In example embodiments, the technology disclosed may be used with a surgical method comprising at least some of the following steps:
 a. attaching a three-dimensional engagement surface of a patient-specific saw guide to a corresponding surface of a tibia of a patient for whom the saw guide is customized by computer imaging during a pre-operative planning stage, the three-dimensional engagement surface conforming as a negative surface to the corresponding surface of the patient's tibia;
 b. drilling, or predrilling, at least one fixation hole through the tibia bone;
 c. making a partial bone cut in the tibia through an opening of the saw guide, the slot oriented at a patient-specific angle relative to an anatomic axis of the patient, the angle custom-selected during the pre-operative planning stage for correcting the patient's anatomy;
 d. loosening, by use of an osteotome, a bone segment defined by the partial bone cut;
 e. removing the bone segment, or cut out piece of the tibia, to obtain access to the dome of the talus;
 f. drilling a hole in the dome of the talus for the peg and the shallow hole for the cap of an implant;
 g. inserting an implant into the dome of the talus; and
 h. refixating the bone fragment in its original position with the aid of surgical screws inserted into the pre-drilled holes.

The patient-specific osteotomy kit of the technology disclosed may also include patient-specific fixation means in form of e.g. screws such as titanium screws, which have a certain diameter and a certain length configured to allow for a correct, or predetermined, refixation of the temporarily removed bone fragment, e.g. a length corresponding or adapted to the depth of the holes predrilled through the bone fragment and beyond the saw cutting plane into the inner portions of the tibia.

The osteotomy surgical kit can also include saw blades configured to allow for a predetermined cutting length corresponding to a cutting depth, in order to avoid unintentionally sawing too deep and thereby damaging the articular surface of the talar dome. The cutting depth can be determined at the pre-operative planning stage. In various other embodiments, the cutting depth of the selected sawblade can be verified using a separate verification tool, e.g. a depth meter tool, which may e.g. have a depth stop. The cutting depth can also be verified by a separate depth meter verification tool having a depth stop with a certain depth adapted to be engaging a powertool at a specific depth and preventing insertion of sawblades that cut beyond a certain depth. Thus, the depth meter verification tool can be used for verifying that the sawblade is restricted to saw cutting to a pre-determined cutting depth which may be patient-specific and determined on the basis of radiologically obtained patient data, such as MR, CT or X-ray imaging.

In the verification process, the saw attachment and sawblade are first attached to the powertool and a verification tool, or depth meter tool, is used to verify that the selected sawblade has the correct dimension for the saw guide. The verification tool is configured with a depth stop designed to be engaging the powertool at a specific depth to prevent insertion of sawblades into the slit of the saw guide that cut beyond a certain length. In example embodiments, the verification process using the depth meter verification tool includes at least some of the following steps:
 The surgeon selects a sawblade that is either commonly used for a specific osteotomy procedure, and/or the surgeon believes have the desired dimensions,
 The dimensions of the sawblade selected by the surgeon are uploaded together with radiologically obtained patient data to the system used for designing the saw guide,
 The saw guide is designed based on the uploaded dimensions of the sawblade and the radiologically obtained patient data,
 Prior to performing surgery, the surgeon uses a verification tool in form of an osteotomy depth meter to verify that the selected sawblade has the correct or desired dimensions for the designed saw guide.

The size and dimension of the portion of the saw guide which comprises the saw cutting slit, and which may correspond to or define the depth of the slit, may be designed to be adapted to the length of the sawblade as the powertool, to which the sawblade is attached, engages and stops at the upper surface of the portion of the saw guide. In certain example embodiment of the method for designing the saw guide, the dimensions, e.g. the depth/height, of the portion of the saw guide comprising the slit may be customized based on the sawblade selected.

BRIEF DESCRIPTION OF DRAWINGS

Embodiments of the disclosure will now be described in more detail with reference to the appended drawings, wherein:

FIG. 4 shows different views of the saw guide according to the disclosure mounted in place on the distal medial end of the left tibia.

FIG. 5 shows a view from another angle with the saw guide 1 mounted in place and more clearly showing the three guide surfaces 2, 3, 4 used for precision cutting a quadrant section of the tibia.

FIG. 6 shows the saw guide in use in making a transverse cut with surgical saw.

FIG. 7 shows a view of the talocrural area with the sawn out corner block of the tibia folded out to expose the talus dome.

FIGS. 8A and 8B show the hollow drill guide included in the surgical kit according to the disclosure.

FIG. 9 shows the drill guide mounted in place on the talus dome.

FIG. 10 shows a patient customized talus implant.

DETAILED DESCRIPTION

The inventors have identified a need for an improved procedure and improved tools aimed at addressing problems related to the technical difficulties of performing a successful oblique osteotomy, such as an oblique medial malleolar osteotomy. These difficulties include sawing at a precise angle that allowed refixation of the distal fragment without creating an articular incongruence, and, for the example embodiment of a medial malleolar osteotomy, identifying the intersection between the tibial plafond and medial malleolus. The technical difficulties that the inventors have identified need to be addressed also include the difficulty of reduction and potential for malunion because apposition may not be collinear with respect to the osteotomy cut. In the example embodiment of a medial malleolar osteotomy, an incongruent joint fixation after refixation of the removed piece of the tibia could lead to secondary osteoarthritis of the ankle joint. The longitudinal, or long, tibial axis can serve as an intraoperative reference to direct the osteotomy. This axis is commonly used for several orthopedic procedures, including total knee arthroplasty and high tibial osteotomy.

The technology disclosed is aimed at providing a more reliable osteotomy procedure by providing the surgical tools enabling a more precise and reliable alignment and identification of desired, or optimal, angles for saw cutting and refixation of the bone fragment, which would be helpful for use during surgery. In this connection, the inventors of the technology disclosed have identified a need for improved surgical tools designed for aiding the surgeon in properly performing the saw cutting and refixation of the removed bone fragment at the desired angles relative certain anatomic landmarks, e.g. the long tibial axis A, including improved tools for aiding the surgeon to perform these tasks in a precise and reliable manner, for optimized resulting osteotomy and to minimize the risks for complications.

Figure 1:
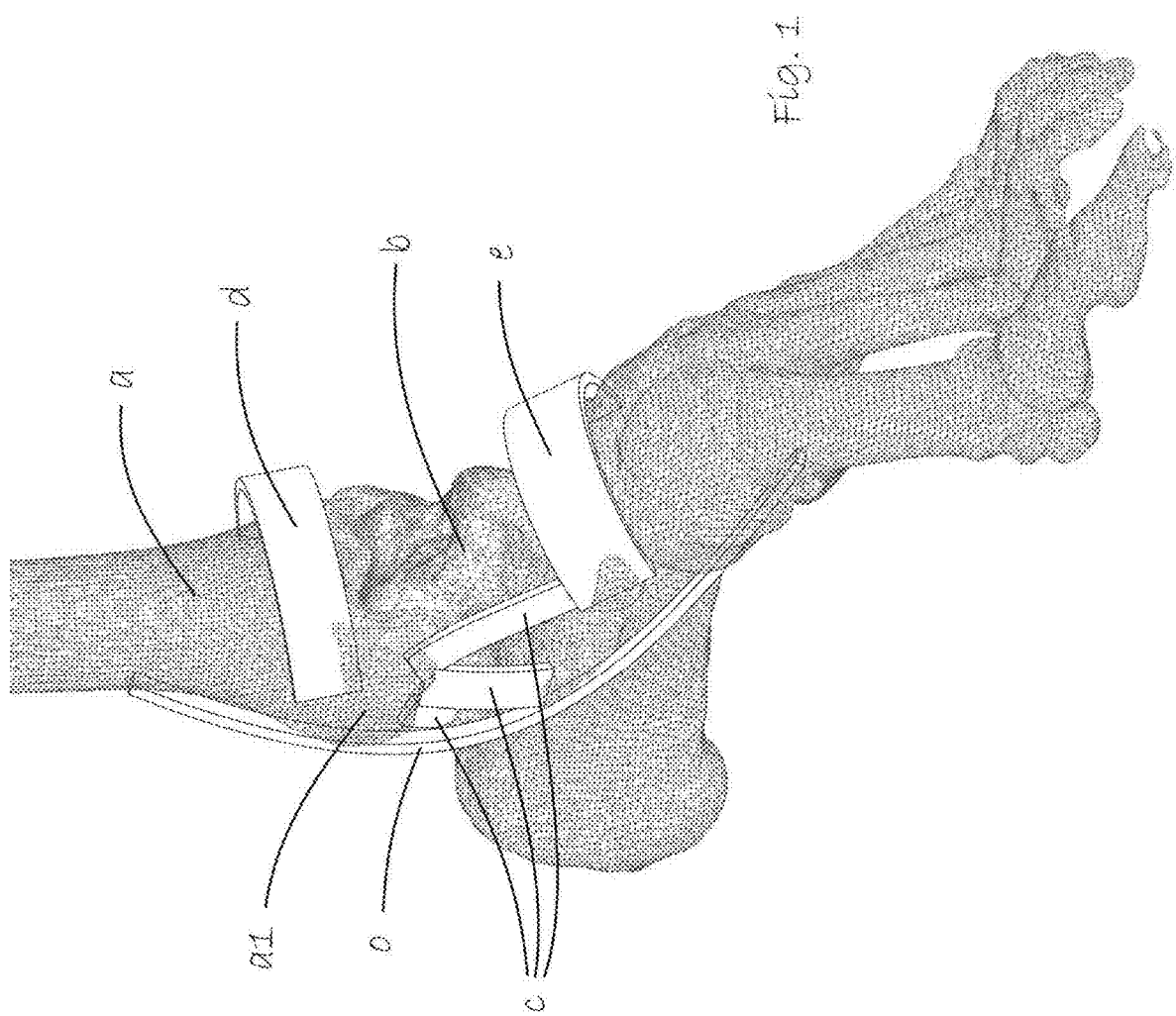
FIG. 1 shows a skeletal view of the foot with ligaments, to illustrate the area of use of the disclosure.

FIG. 1 shows, to show the area of use of the present disclosure, the skeletal foot of a patient to receive a customized surgical implant to repair the condylar dome surface of the talus. The bones and ligaments of the area of the foot where the kit according to the disclosure is to be used constitute, of course, no part of the present disclosure and are therefore labelled with letters. The lower medial end of the tibia a is shown as well as the talus b and, schematically, the medial deltoid ligaments c covering this joint and attached to the malleolus a1. 0 indicates purely schematically the tendons of the flexor digitorum longus and the flexor hallucis longus. d indicates the superior extensor retinaculum.

Figure 2:
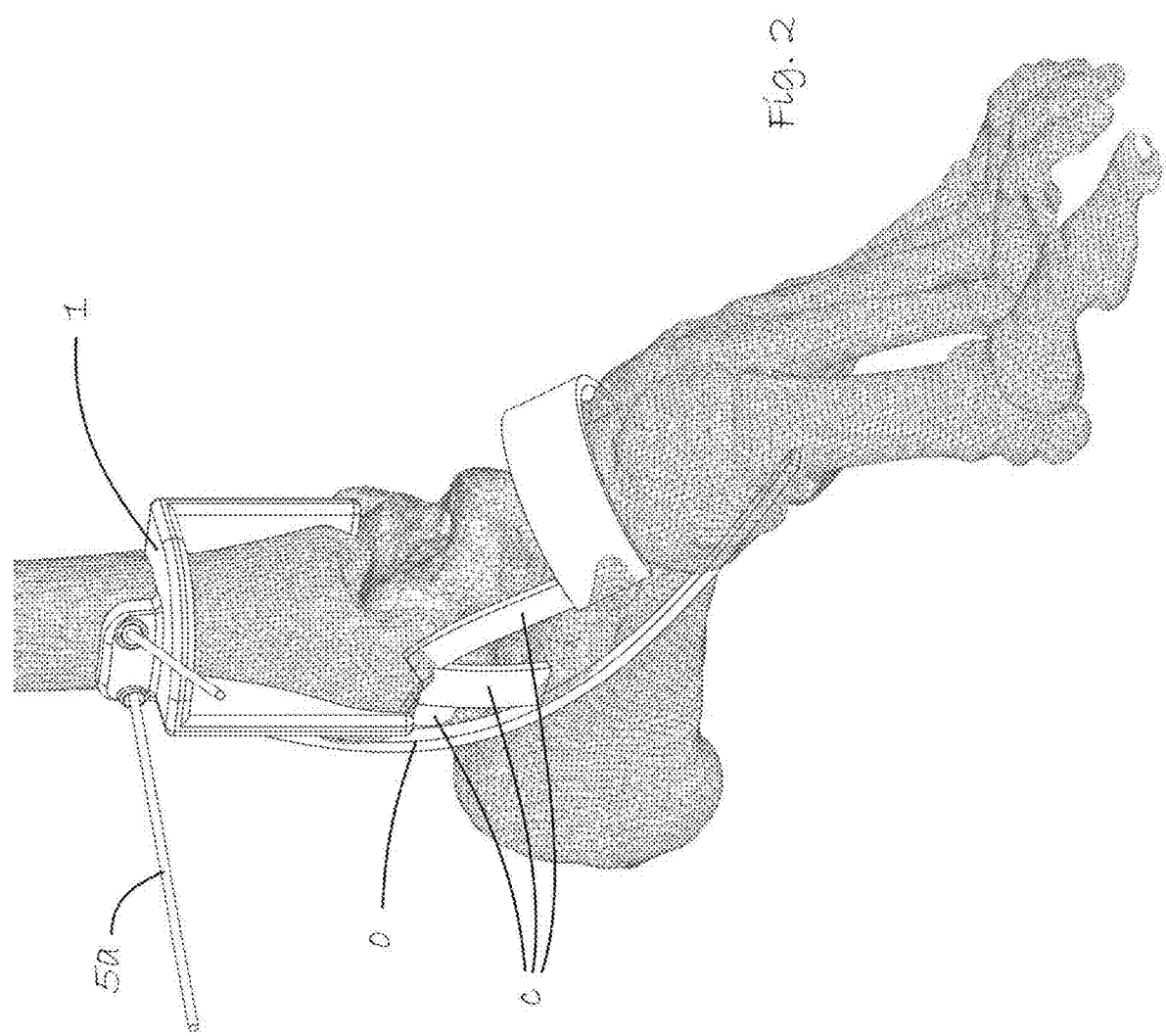
FIG. 2 shows the same skeletal view as FIG. 1 with a saw guide mounted in place.

FIG. 2 shows the same view as FIG. 1 but with a saw guide 1 in a surgical kit according to the disclosure mounted in place on the distal end of the tibia a using pins 5a. The superior extensor retinaculum d shown in FIG. 1 is not shown in this figure. It has been pulled down out of the way of the saw guide using a surgical hook, without any need to cut into this retinaculum.

Figure 3:
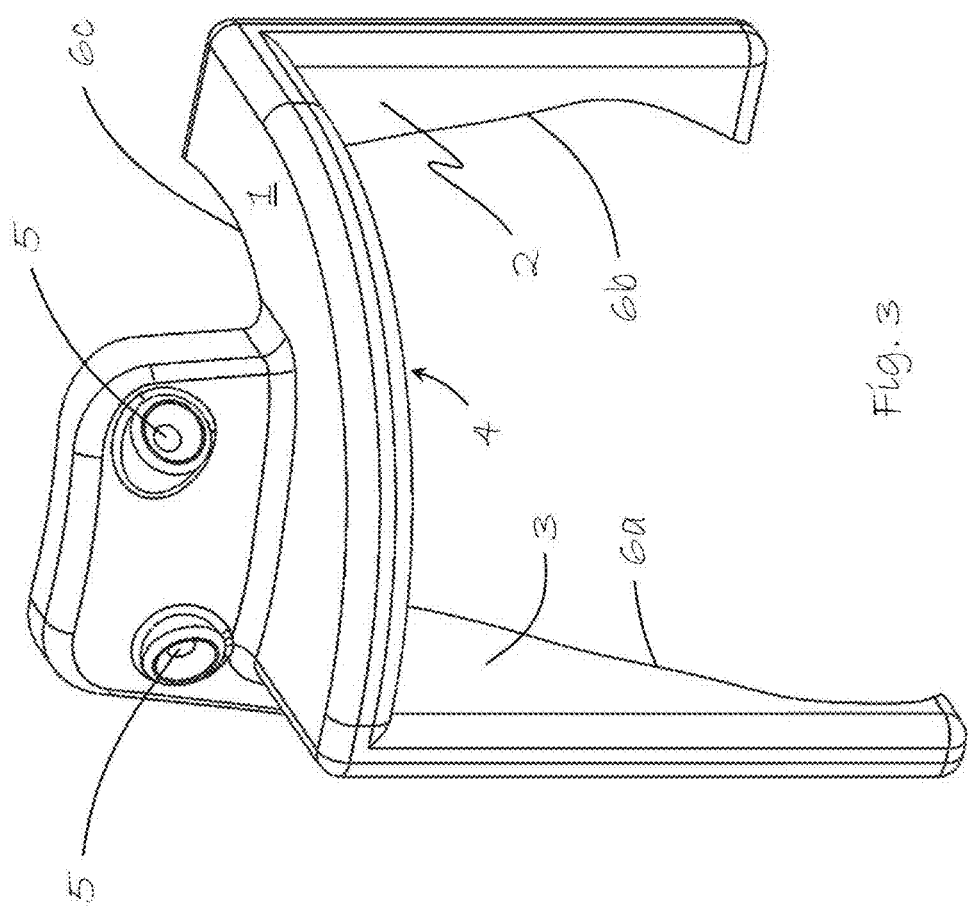
FIG. 3 shows the saw guide of the disclosure and which is included in the kit according to the disclosure.

FIG. 3 shows alone the saw guide 1 of the kit according to the disclosure. Each saw guide is customized via imagery of the patient's tibia through e.g. MRI, CT or X-ray. Each saw guide has surfaces 6a-c conforming to the particular patient's tibia. One of the surfaces 6a is longer to cover the malleolus. In this embodiment, the saw guide 1 provides three saw guide surfaces 2, 3, 4, respectively, in the sagittal, coronal and transverse planes respectively. Two pin holes 5 are provided for securing the saw guide in place on the tibia.

The saw guide is individually made specific to the patient's specific anatomy and to the specific damage to the talus, possibly through the following saw guide design steps:

a. identifying a subchondral damage of the talus dome through radiological images such as MR, CT or X-ray images or through arthroscopy.

b. planning the size and the location of an osteotomy needed to get access to the talar dome in order to treat the subchondral damage c. creating a 3D model of the tibial bone from radiological images such as MR, CT or X-ray images d. virtually designing a patient specific osteotomy guide based on the 3D model of the tibial bone and the size and location of the osteotomy needed.

FIG. 4 is a close-up view of the saw guide put in place on the lower end of the tibia in an initial stage of the procedure utilizing the kit according to the disclosure. The skin has first been pulled away exposing the anterior medial area of the tibia where the patient customized saw guide is to be mounted. Pins 5a are driven into the bone through the pin holes 5 at different angles to fix the saw guide securely in place.

FIG. 5 shows a view from another angle with the saw guide 1 mounted in place and more clearly showing the three guide surfaces 2, 3, 4 used for precision cutting a quadrant section of the tibia to expose the dome of the talus.

FIG. 6 shows use of a surgical saw 7 to make a transverse cut along the guide surface 4 using inserted pins 5a to prevent the cut from penetrating deeper than intended. A form-fitting thin talus guide (not shown) is slipped in between the tibia and the talus to protect the talus as cuts are made along the guide surfaces 2 and 3. The quadrant section of the tibia is finally removed by a flat surgical chisel cutting any remaining bone material in the inner corner.

Referring now to FIG. 7, the sawn out bone quadrant of the tibia is then folded forwardly and outwardly taking care not to damage the medial deltoid ligaments c continually attached between the bone quadrant of the tibia and the talus b. The talus dome is thus exposed. The dome area to be repaired with the implant is labelled b1.

FIGS. 8A and 8B show alone one exemplary drill guide 10 in the kit according to the disclosure. A drill sleeve (not shown) is inserted into the hollow center of the drill guide, fitting into the height adjustment sprockets 12 at the top of the interior 11 of the drill guide. The lower surfaces of the drill guide conform to the condylar surfaces of the talus which are to be provided with a replacement implant. A saddle shaped flange 15 conforming to the ridge of the talus dome of the particular patient extends from the drill guide cylinder. The flange has medial and lateral pin holes, 14a and 14b respectively, for securely mounting the drill guide in place on the talus dome. It is also possible, in a non-limiting embodiment, to provide the saddle shaped flange 15 with a downwardly bent corner portion or hook 16, disposed at the lateral pin hole 14b. This corner hook portion 16, which is most visible in FIG. 8B, is designed to help in correctly positioning and anchoring the drill guide on the neck of the talus b. The entire drill guide and in particular the surface of the saddle shaped flange 15 is individually dimensioned to the patient's talus. The saw guide 1 is dimensioned to provide, with only three saw cuts a tibia quadrant piece which when folded out provides enough space for the drill guide 10 and for vertical downward drilling so that the peg will be mounted coaxial or close to coaxial to the downward forces exerted, when walking, by the end of the tibia against the implant, with no lateral forces tending to dislodge the implant over time.

FIG. 9 shows the drill guide fixed in place on the dome of the talus. Just a large enough quadrant section of the tibia has been sawn out to make room for the drill guide and the room needed to use the guide, now placed directly over the area of the talus to be repaired. The drill guide is also directed so as to provide the correct angle for the peg of the implant so that the angle of the peg ideally is aligned with the forces exerted by the tibia when walking.

FIG. 10 shows in detail a patient customized implant 20 made in a biocompatible metal, metal alloy or ceramic. More specifically it may comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia.

The implant has typically a cap diameter of 12 or 17 mm or even 20 mm, but may also assume other diameters within this range.

The implant has a cap 21 having a top surface 22, comprises a cobalt chrome alloy (CoCr) or stainless steel, diamond-like carbon or a ceramic and the top surface 22 has been custom surfaced to match the undamaged talus dome of the particular patient. The implant has a cap 21 with on its outside a new joint surface and on its inside, in this particular embodiment, a bone facing surface with a ridge 24 which lodges in a drilled groove as will be explained below.

Extending downwardly perpendicularly and centrally from the cap 21 is a mounting peg 23, for insertion into a hole drilled in the talus dome.

This individually shaped implant can be made on the basis of CT-scans, MR-imaging or X-ray images, by the method described in Application No. PCT/EP2014/064749.

Figure 11:
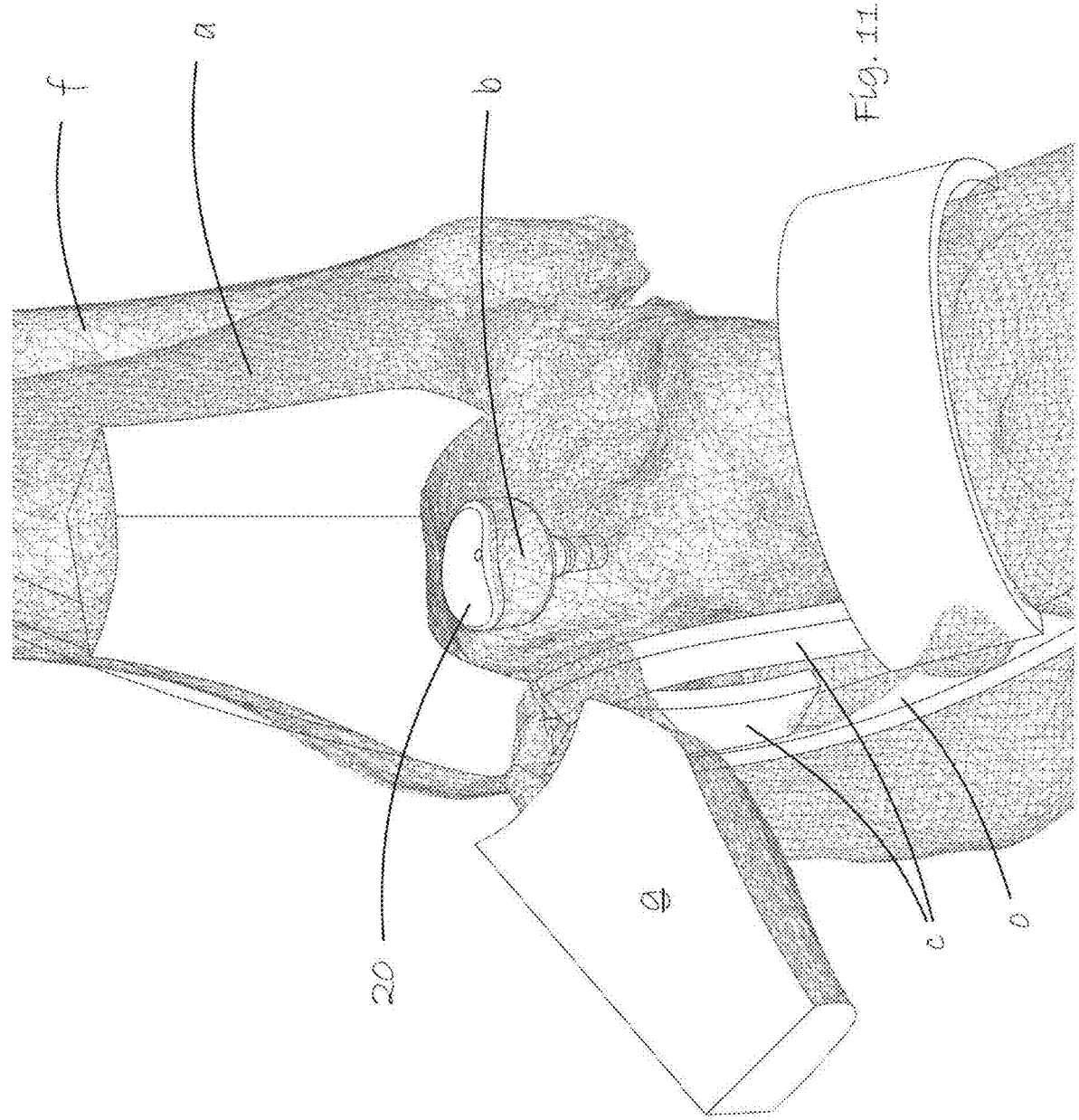
FIG. 11 shows the talus implant hammered into place in the talus dome, replacing the damaged surface of the talus joint.

FIG. 11 shows the implant 20 in its final placement after being hammered down into its hole, whereby the peripheral rim around the lower surface of the cap lodges in a groove in the hole in the talus. The cut out tibia bone quadrant piece g is still folded out. The quadrant piece g is then folded back into its original position and screwed into place preferably using two titanium screws into either vertical surface. According to a preferred operational method, the two screw holes are pre-drilled through the quadrant piece and into the tibia, before the saw cuts are made to make sure that the tibia quadrant piece will be remounted in exactly its original position.

Figure 12:
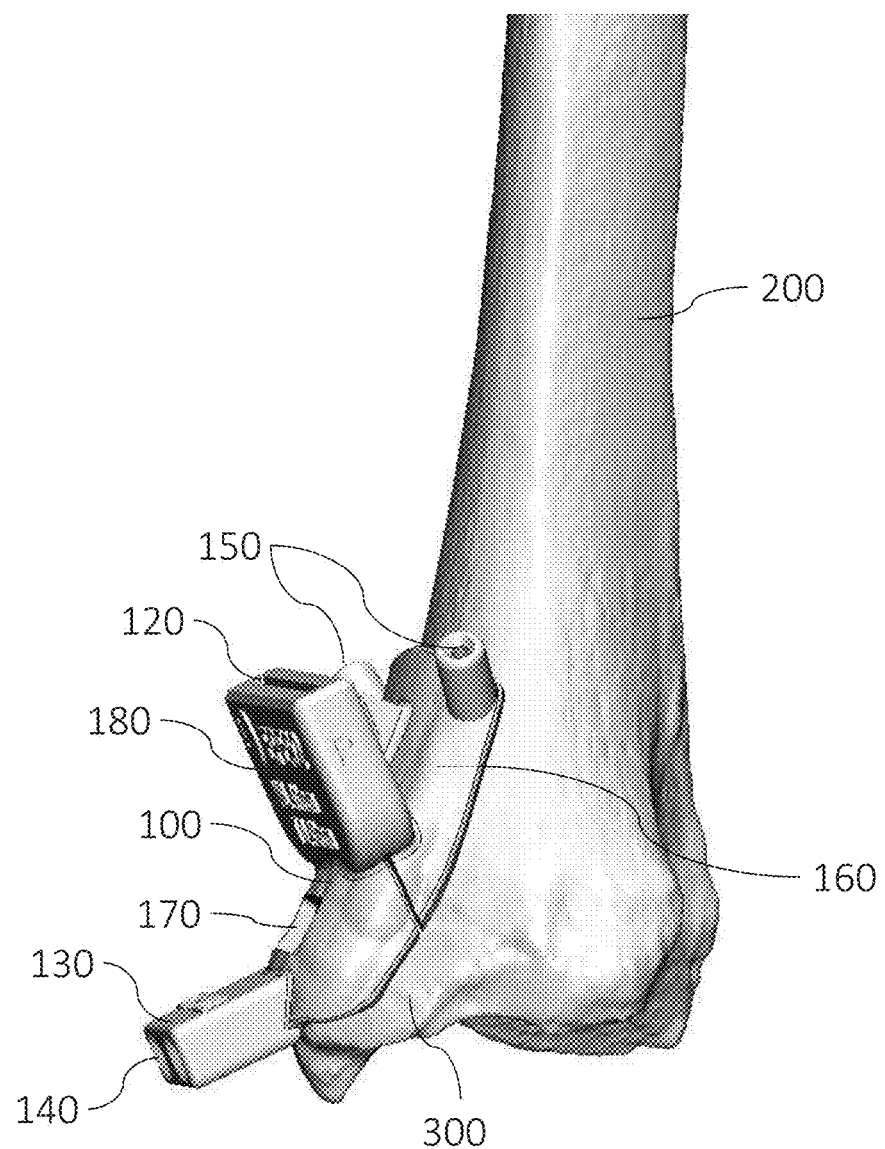
FIG. 12 shows a visualization of a saw guide placed on the distal tibia of a patient, according to one or more embodiments.

FIG. 12 shows a saw guide 100 placed on an example area of use of the technology disclosed in form of the lower tibia of a patient to receive surgical treatment to repair the condylar dome surface of the talus. The bones and ligaments of the area of the foot where the kit and saw guide according to the disclosure is to be used constitute, of course, no part of the present disclosure and are therefore labelled with letters. The lower medial end of the tibia 200 is shown as well as the malleolus 300.

Figure 13:
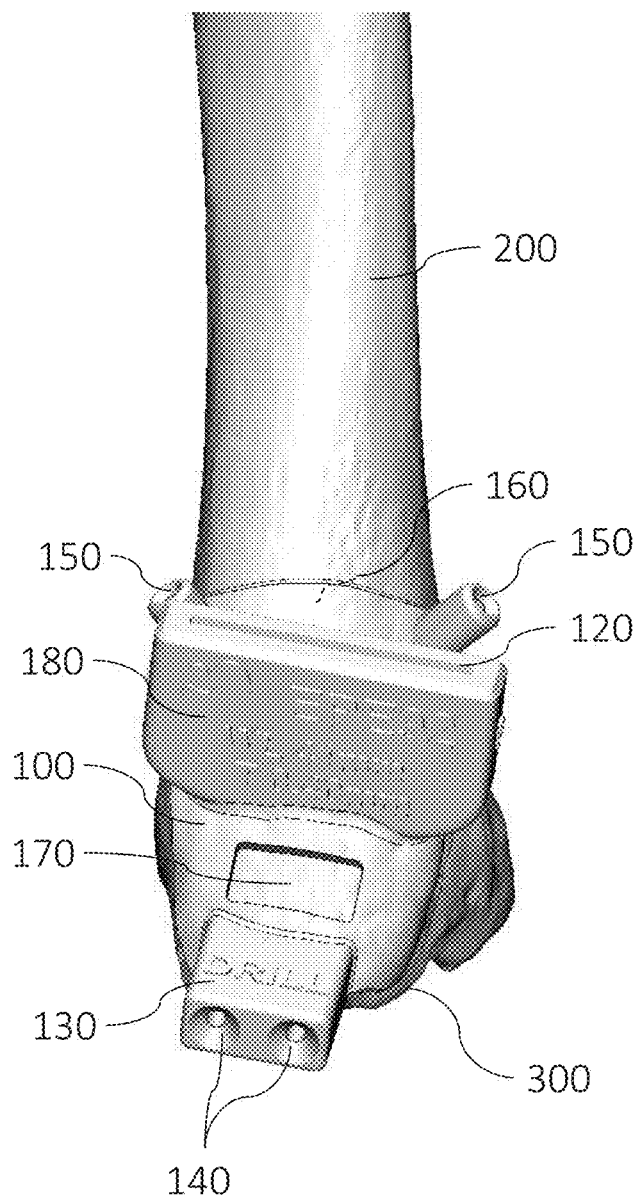
FIG. 13 shows the same example saw guide placed on the distal end of the tibia as FIG. 12, but from a different angle, according to one or more embodiments.
Figure 14:
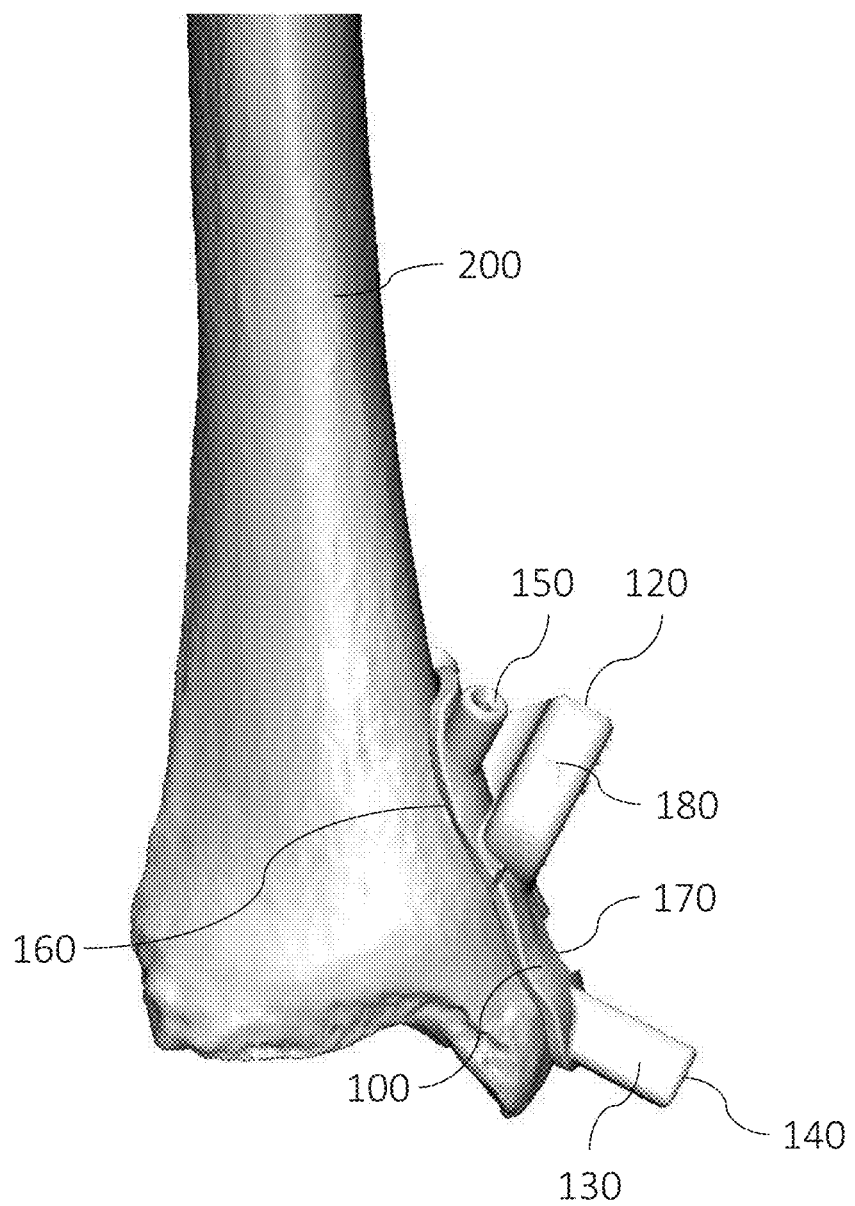
FIG. 14 shows the same example saw guide placed on the distal end of the tibia as FIG. 12, but from a different angle, according to one or more embodiments.

FIGS. 13 and 14 show the same example saw guide 100 placed on the distal end of the tibia as FIG. 12, but from a different angle.

Figure 15A:
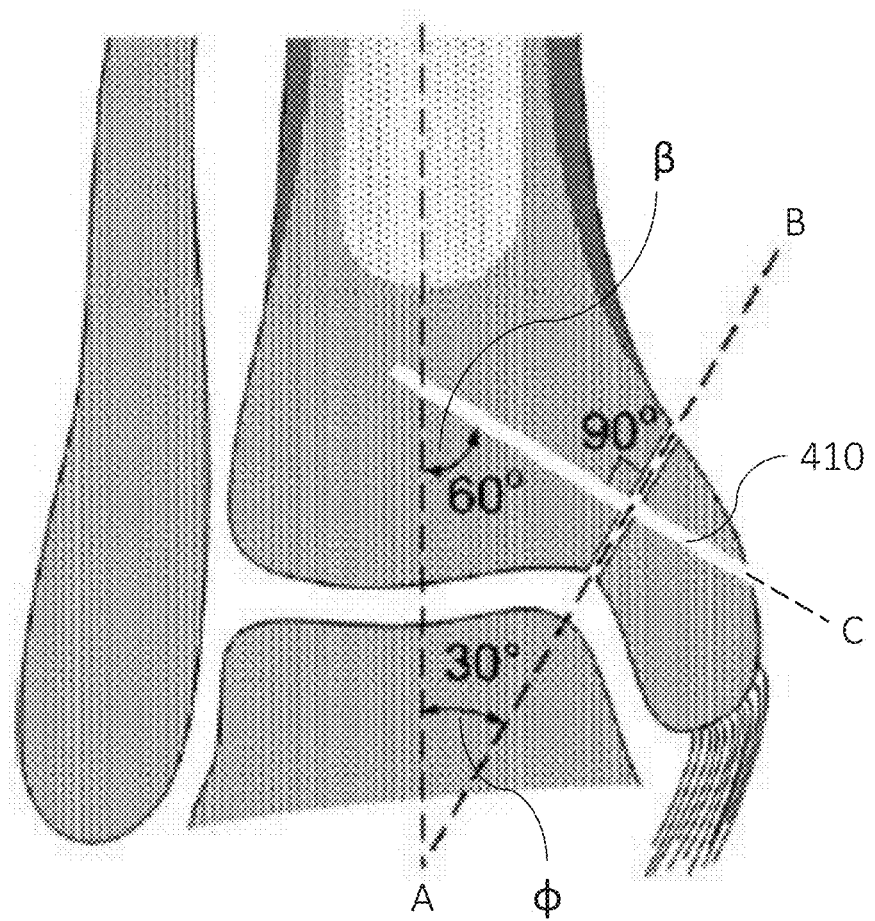
FIG. 15a illustrates an example embodiment of the technology disclosed where the osteotomy saw cut is made at a 30 degrees angle to the longitudinal tibial axis and the drilling of fixation holes is made at a 60 degrees angle to the longitudinal tibial axis.
Figure 15B:
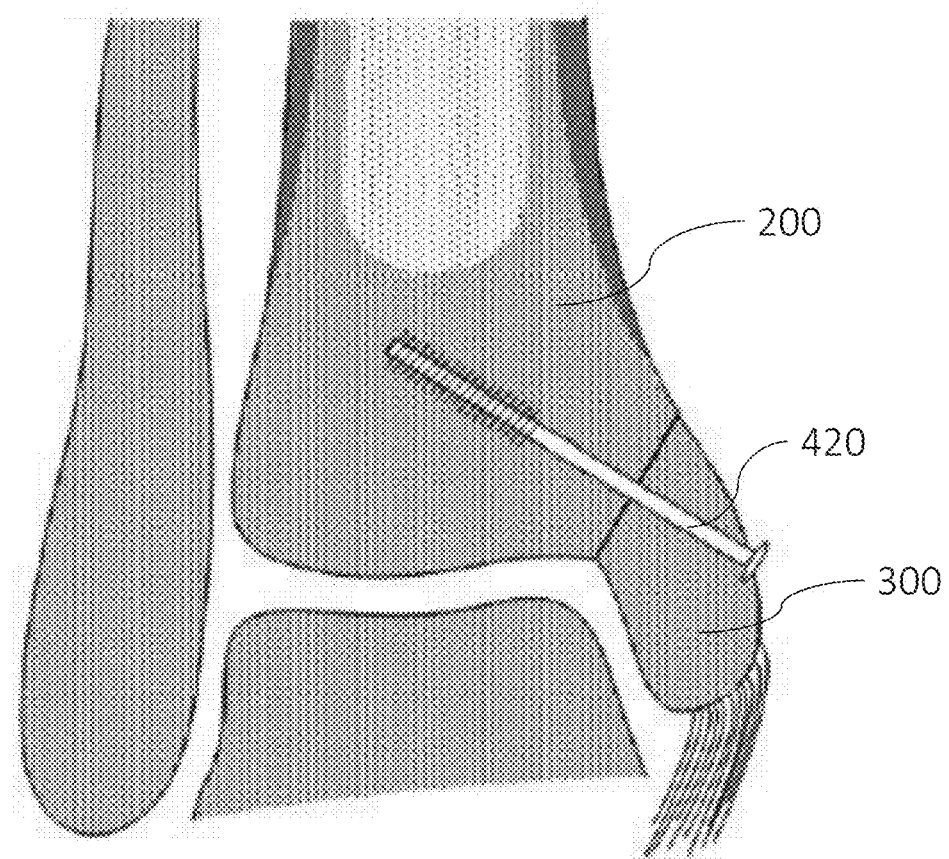
FIG. 15b illustrate the example embodiment of an osteotomy of FIG. 15a and the refixation of the temporarily removed bone fragment at approximately a 60 degrees angle to the longitudinal tibial axis, by the use of fixation means such as e.g. at least one screw.

FIGS. 15a and 15b illustrate an example embodiment of the technology disclosed aiming at avoiding an articular step off after refixation through predrilled fixation holes 410, screw holes. FIG. 15a illustrates that, after predrilling the fixation holes 410, or screw holes, at 60 degrees angle β in relation to the long tibial axis A, the osteotomy is made at 30 degrees angle in relation to the long tibial axis A. In FIG. 15a, the single saw cut is made in a direction B, or axis B, at an angle φ relative to the reference axis A in form of the longitudinal tibial axis, and the drilling is made in a direction C, at an angle β relative to the longitudinal tibial axis. FIG. 15b illustrates that the introduction of the compression screws through the predrilled holes, which are illustrated in FIG. 15a, will result in a smooth joint surface.

The single saw cut may be selected at an angle φ relative to a selected reference axis A, another angle direction defined by the saw guide or at least a portion of surface of the saw guide or the patient. In the example embodiment of the technology disclosed illustrated in FIGS. 15a and 15b, the reference axis A is in form of the longitudinal tibial axis of a patient and, in this example, the single saw cut is made in a first direction B at an angle φ which is 30 degrees in relation to the longitudinal tibial axis A. In this example, the drilling, or pre-drilling, of the at least one fixation hole is made in a second direction C at a second angle which is 60 degrees in relation to the long tibial axis A. In this example of the technology disclosed, the first angle φ and the second angle β to the longitudinal axis A have a sum of 90 degrees. The saw guide according to example embodiments of the technology disclosed is provided with a drill guide comprising at least one hole which is configured with an orientation adapted to guide drilling in a perpendicular direction, or close to 90 degrees, with respect to the direction for forming said single saw cut. The first reference axis A can also be another selected anatomic axis. Other anatomic axes, such as axes having significantly different orientations than the orientation of axis A illustrated in FIGS. 15a and 15b, can be used as reference axes.

The saw guide 100 according to embodiments of the technology disclosed comprises, as an integral part, a drill guide 130 having at least one hole 140 with a certain diameter, depth, orientation and position on the saw guide to thereby be adapted for guiding the drilling in a direction at a precise and desired or optimal angle, e.g. relative the long tibial axis A, and which thereby has the additional advantage of preserving the deltoid ligament that originates more distally yet avoiding screw placement that can cause disruption of the deltoid ligament. A surgical kit including a saw guide comprising a drill guide 130 according to the technology disclosed makes this possible in a precise and reliable manner, providing for a precise and reliable pre-drilling operation which would be almost impossible to achieve with a free-hand predrilling procedure, or when the saw cutting procedure and the predrilling and refixation procedure are essentially two separate procedures which are not strongly linked to each other. The surgical kit according to the disclosure may, in addition to the saw guide 100, be comprised of fixation screws 420 with dimensions, a diameter and a length configured to be used for screwing through the at least one hole 140 of the drill guide 130 and sawblades 190 with dimensions, a diameter and a length suitable for saw cutting through the slit 120. In certain example embodiments, the surgical kit may, in addition to the saw guide 100 for assisting the surgeon in osteotomy procedure of a first bone structure, also include at least one of a surgical implant, a dummy implant, a drill, a mandrel and a second drill guide in form of a hollow tubular shell 620 used for drilling of the damaged area on the articular surface of a second bone structure in the surgical procedure of implantation of resurfacing inlay implants. The mandrel may be used to gently tap down the surgical implant into the bone until bottomed.

The at least one hole 140 of the drill guide 130 may be used to guide the predrilling of at least one fixation hole to be used for refixation of the removed bone fragment after surgical treatment of e.g. a bone fracture, a damaged cartilage and/or a tissue. The predrilling of the at least one fixation hole has the purpose of facilitating the correct refixation of the bone fragment to the first bone structure. The saw guide may further comprise at least one pin hole 150, or first opening, adapted to receive a fixation means 510, such as a pin, where the at least one pin hole 150 have an orientation adapted to guide the temporary fixation of the saw guide to the first bone structure of a patient. The at least one pin hole 150, or first opening, is provided for securing the saw guide in place on the first bone structure during both the predrilling and the saw cutting. The at least one hole 140 of the drill guide 130 may be used to guide the pre-drilling of at least one fixation hole 410 to be used for refixation of the removed bone fragment after surgical treatment. The pre-drilling of the at least one fixation hole 410 has the purpose of facilitating the correct refixation of the bone fragment. The at least one pin hole 150, or first opening 150, is provided for securing the saw guide 100 in place on the tibia during both the pre-drilling and the saw cutting.

In example embodiments of a method for designing the saw guide 100 suitable for use in osteotomy and the temporary osteotomic removal of a bone fragment of a first bone structure of a patient for exposing a second bone structure for surgical treatment, the portion 180 of the saw guide comprising said slit 120, or opening may be designed with a height that matches, or corresponds to, the length of the sawblade 190 to be used during sawing to thereby make the powertool 520 used during sawing stop against the top surface of the portion 180, thereby minimizing the risk of unintentionally sawing too far, e.g. into the articular surface of the second bone structure. In certain example embodiments, the dimensions of the portion 180 of the saw guide, e.g. the height, may be customized, e.g. via imagery of at least one of a first and second bone structure of the patient through e.g. MRI, CT or X-ray and/or based on the sawblade selected. As an example, the length of the sawblade and/or the thickness of the malleolus of a specific patient may be used to determine the height of the portion of the saw guide.

In accordance with certain aspects and in a preferred osteotomy procedure aimed at gaining access to the dome of the talus, a predrilling to create fixation holes to be used for refixation of the removed bone fragment is preferably performed before the saw cutting. The pre-drilling is performed through and past the saw cutting plane B defining the bone fragment to be cut out and removed and into the bone there behind, thereby creating predrilled fixation holes in the inner portions of the tibia bone which will remain in the inner portion of the tibia bone when the bone fragment is temporarily removed. As of today, the saw cutting procedure and the predrilling procedure are essentially two separate procedures which are not strongly linked or interrelated to each other.

The slit, or opening, and the portion 180 of the saw guide comprising said slit, may be configured to be used to form a single saw cut in the removal of a bone fragment of the tibia to gain access to the medial talar dome of the ankle joint for a specific treatment of damage to the cartilage and/or bone of the talus. In example embodiments of the technology disclosed, the portion 180 of the saw guide comprising said slit 120, or opening is designed with a height that matches, or corresponds to, the length of the sawblade 190 to be used during sawing to thereby make the powertool 520 used during sawing stop against said portion 180, thereby minimizing the risk of unintentionally sawing too far, e.g. sawing into the articular surface of the talus. The at least one hole of the drill guide of the above saw guide may be configured to guide the drilling, or pre-drilling, of at least one hole through the bone fragment, or piece of the tibia, to be removed, past the single saw cutting plane provided by the guidance of said slit 120 and into the inner portions of the tibia there behind, thereby being adapted to provide for the pre-drilling of at least one fixation hole 410 which can be used for facilitating correct refixation of the removed bone fragment in its original, or substantially original, position after performed treatment, e.g. surgical treatment, by the use of fixation means 420, e.g. in the form of at least one screw. The fixation means 420 are inserted through the bone fragment to be removed and into the inner portions of the tibia through the pre-drilled at least one fixation hole 410, thereby fixing the temporarily removed bone fragment to the inner portions of the tibia.

The size and dimension of the portion 180 of the saw guide 100 which comprises the saw cutting slit, and which may correspond to or define the depth of the slit 120, may be designed to be adapted to length of the sawblade 190 as the powertool 520, to which the sawblade 190 is attached, engages and stops at the top surface of the portion 180 of the saw guide. In certain example embodiment of the method for designing the saw guide, the dimensions of the portion 180 of the saw guide 100 may be customized based on the sawblade selected.

The saw guide 100 is designed to improve the procedure for refixation of the bone fragment by providing improved surgical tools for a more precise and reliable procedure for the predrilling of at least one fixation holes past the bone fragment to be removed and into the bone there behind. The drilling, or predrilling, of the at least one fixation hole 410 has the purpose of facilitating the correct refixation of the temporarily removed bone fragment, thereby increasing the likelihood of preserving the deltoid ligament that originates more distally, yet reducing the risk for a drilling that can cause severing of any muscles, tendons and ligaments. If the at least one fixation hole 410 is predrilled at a less desirable angle relative certain anatomic landmarks in a direction so that the at least one screw 420 is inserted either more horizontally or more vertically than optimal, an intra-articular step off might result. A screw placement which is too vertical may also cause disruption of the deltoid ligament. In this connection, an important aspect of the technology disclosed is that the predrilling of the at least one fixation hole 410 enables a correct positioning of the removed bone fragment in its correct original, or substantially original, position to create a congruent joint surface for better healing. According to the technology disclosed, the predrilling at a desired position and angle direction relative an anatomy landmark of a patient is determined by the position for the placement of the saw guide 100 on the surface of a first bone structure, e.g. the distal end of the tibia, and the fixed angular and positional relationship between the position and orientation of the slit 120 on the saw guide 100 and the position and orientation of the at least one hole 140 of the drill guide 130 on the saw guide 100. The saw guide 100 according to the technology disclosed, having a drill guide 130 with its at least one hole 140 as an integral part, thereby enables a precise and reliable positioning of the removed bone fragment in its original, or substantially original, position to create a congruent joint surface for better healing. In certain embodiments of the technology disclosed, the inner engagement surface 160 and/or the fixed angular and positional relationship between the position and orientation of the slit 120 and the at least one hole 140 of the drill guide 130 of the saw guide 100 is patient-customized on the basis of radiologically obtained patient data, such as MR, CT or X-ray imaging.

The improved saw guide according to the technology disclosed comprises, as an integral part, a drill guide 130 having at least one hole 140 with a certain diameter, orientation and a position configured for guiding the drilling in a direction at a precise and optimum angle, e.g. relative the long tibial axis A. The introduction of a saw guide which comprises a drill guide as an integral part and thereby provides a fixed angular relationship between the orientation and position of the at least one hole of the drill guide and the engagement surface 160 of the saw guide and the orientation of the slit 120, or opening, for guiding the saw cutting enables a fast osteotomy procedure including a more precise and reliable predrilling operation. A more precise and reliable predrilling operation gives the advantage of increasing the likelihood of preserving the deltoid ligament that originates more distally, yet avoiding screw placement that may cause disruption of the deltoid ligament. The present disclosure further provides different method for designing a saw guide 100 having a drill guide 130 as an integral part and with a fixed angular and positional relationship between orientation and position of the at least one hole 140 of the drill guide 130 for guiding the direction of the drilling, or predrilling, and the orientation of the slot 120, or opening, for guiding the direction of the saw cutting.

Certain embodiments provide for a saw guide which comprises as integral parts both a slit configured to guide the saw cutting in a first direction and a drill guide having at least one hole configured to guide the predrilling in a second direction different from the first direction, where at least some of the features of the saw guide is individually patient customized on the basis of radiologically obtained patient data, such as MR, CT or X-ray imaging.

In certain embodiments, a method for designing a saw guide 100 is provided which comprises as integral parts both a slit 120 configured to guide the saw cutting in a first direction and a drill guide 130 having at least one hole 140 configured to guide the pre-drilling in a second direction different from the first direction, where at least some of the features of the saw guide are individually patient customized on the basis of radiologically obtained patient data, such as MR, CT or X-ray imaging. In example embodiments, the method for designing the saw guide comprises designing the inner engagement surface 160 and/or the fixed angular and positional relationship between the position and orientation of the slit 120 and the at least one hole 140 of the drill guide 130 of the saw guide 100 to be patient-customized on the basis of radiologically obtained patient data, such as MR, CT or X-ray imaging. According to certain example embodiments, the method includes designing the at least one hole 140 of the drill guide 130 to have a position and orientation on the saw guide 100 that guide the drilling, or pre-drilling, to be performed at a desired position and angle relative to other features of the saw guide and/or an anatomy landmark of a patient. The method for designing a patient customized saw guide 100 based on radiologically obtained patient data, such as MR, CT or X-ray imaging may be used for at least one of determining a patient-unique inner engagement surface of the saw guide, the position for the placement of the saw guide 100 on the surface of a first bone structure, e.g. the distal end of the tibia, and/or the fixed angular and positional relationship between the position and orientation on the saw guide 100 for the slit 120 and the position and orientation on the saw guide 100 for the at least one hole 140 of the drill guide 130. The patient-customized design of the saw guide 100 according of the technology disclosed, having a drill guide 130 with its at least one hole 140 as an integral part, thereby enables a precise and reliable positioning of the removed bone fragment in its original, or substantially original, position to create a congruent joint surface for better healing. In certain embodiments of the technology disclosed, the inner engagement surface 160 and/or the fixed angular and positional relationship between the position and orientation of the slit 120 and the at least one hole 140 of the drill guide 130 of the saw guide 100 are patient-customized.

In certain embodiments, the present disclosure provides a surgical kit including a saw guide designed to improve the precision and reliability of the combined predrilling, saw cutting and refixation procedures of osteotomy used in surgical treatment.

In order to obtain a congruent joint surface after refixation, the osteotomy is preferably directed at an essentially perpendicular angle relation, or at least within an angle range of 60 to 90 degrees, to the articular surface of the tibia at the intersection between the tibial plafond and medial malleolus so that the saw cutting avoids all important tendons, muscles and ligaments as well as the anterior tibial artery. According to certain aspects of the technology disclosed, the saw guide 100 is designed so that the osteotomy is aimed at 30 degrees relative to the long tibial axis, or at least within an angle range of 15-50 degrees relative to the long tibial axis A. The saw cutting direction is then preferably essentially perpendicular, or at least within an angle range of 60 to 90 degrees, to the articular surface of the tibia and directed at the intersection of between tibial plafond and articular facet of the medial malleolus. Applying this osteotomy direction minimizes the occurrence of a step off at the articular surface after reduction. A medial malleolar osteotomy directed at 30 degrees relative to the tibial axis A enters the joint perpendicular to the tibial cartilage, and will likely result in a congruent joint surface after reduction.

The inventors of the technology disclosed have identified shortcomings associated with the currently used procedure of free-hand drilling and sawing cutting in that these two operations are not strongly linked to each other. The osteotomy procedure used today therefore does not allow for sufficiently precise and reliable drilling and sawing cutting operations at desired positions and angles that allow for a sufficiently accurate refixation of the temporarily removed distal fragment without creating an articular incongruence.

An improved accuracy in the angle of the osteotomy and the direction of drilling relative to an anatomic landmark, e.g. to the longitudinal tibial axis A or the articular surface of the tibia, would be helpful for use during surgery. Currently used surgical tools for osteotomy do not provide for sufficiently precise and reproducible accuracy in the saw cutting and direction of drilling for fixating the saw guide 100, which can lead to severing of muscles and tendons creating exceptional and sometimes permanent problems. Specifically, damage to muscles and tendons caused by the currently used surgical tools and inaccurate osteotomic procedure of free-hand drilling, i.e. where the drilling direction for fixating the saw guide is not directly linked to the saw cutting plane B and/or the anatomy of the patient, may lead to severe problems as regard to repair and rehabilitation.

A saw guide 100 according to the technology disclosed, which in addition to a saw cut opening 120 adapted for providing saw cutting also comprises a drill guide that is an integral part of the saw guide, is configured to enable a precise and reproducible accuracy in the angle direction of drilling of the at least one fixation screw 420 along a straight line which would be almost impossible to achieve with prior art solutions where the drilling of the fixation screws is made by free-hand, or with an osteotomy where the saw cutting procedure and the predrilling and refixation procedure are essentially separate procedures which are not strongly linked to each other.

The inventive concept of the present disclosure, where the drill guide 130 with its at least one hole 140 is made an integral part of the saw guide 100 and thereby provides for a fixation of the saw guide at a fixed angle direction with respect to the saw cutting plane B provided by the saw cutting opening of said same saw guide, mitigates the risk for the osteomtomic procedure causing disruption of the deltoid ligament, or result in an incongruent joint surface after reduction.

According to certain embodiments, the saw guide 100 is patient customized via imagery of the patient's tibia through at least one radiological image, e.g. an MRI, CT or X-ray image, thereby providing for a patient customized saw guide that have a surface conforming to a certain patient's tibia. This patient customized saw guide may then preferably comprise both a saw cut opening adapted to guide the saw cutting in one saw cutting plane B only and a drill guide with at least one hole configured to provide for drilling in a direction, or along an axis C, at an angle to the one saw cutting plane B. Because the surface of the saw guide is designed based on radiological images of the patient's tibia and both the saw cutting plane B and the direction for drilling provided by the saw guide may be set to be in a fixed angle relation to the patient customized saw guide surface, both the saw cutting plane B and the drilling direction may therefore be determined based on said at least one radiological image of the individual patient's tibia when said saw guide is placed in position and conforms to the articular surface.

In certain other aspects of the technology disclosed, at least one of the saw cutting opening providing for the saw cutting plane B and the at least one drilling hole 410 of the drilling guide providing for the direction for drilling at least one fixation means 420, or screw, for refixation of the saw guide to the tibia 200, may be determined based on at least one radiological image of the patient's tibia, e.g. an MRI, CT or X-ray image. In certain configurations of a patient customized saw guide and methods for designing such a saw guide, the saw cutting opening and the at least one drilling hole are both designed based on at least one radiological image of the patient's tibia in that a patient customized angle relationship between at least one of the one saw cutting plane B and the drilling direction along a straight line, or axis C, for fixating the saw guide to the tibia 200, is determined based on said at least one radiological image. In yet another example of a saw guide and method for designing the saw guide according to the technology disclosed, at least one of the angle relation between the saw cutting plane B provided by the saw cutting opening to the longitudinal axis of the patient's tibia and the angle relation of the drilling direction to the longitudinal axis of the patient is determined based on said at least one radiological image of the patient.

Any severing of muscles and tendons to gain access to a second bone structure through an osteotomic procedure of a first bone structure will create exceptional and sometimes permanent problems as regards repair and rehabilitation.

It is thus necessary to expose the second bone structure by drilling the fixation holes and cutting out a portion of the first bone structure, under a number of difficult constrictions:
  avoiding all important tendons, muscles and ligaments and leaving them attached and intact,
  avoiding any arteries of the first bone structure,
  providing enough exposed space to correctly perform a surgical treatment of at least one of a bone and a cartilage damage of the second bone structure,
  making the drilling of the fixation holes and the sawing of the bone cut precise and correct on the first try, facilitating a correct refixation of the temporarily removed bone fragment in its original position for healing.

The anatomy of the talocrural area differs from that of e.g. the knee in that it is very difficult for the surgeon to access the dome of the talus. It is covered by the lower condylar surface of the tibia, as well as being encased by a many different muscles, tendons and ligaments. Any severing of these muscles and tendons to gain access to the talus dome will create exceptional and sometimes permanent problems as regards repair and rehabilitation.

The longitudinal tibial axis A can serve as an intraoperative reference to direct the medial malleolar osteotomy. This axis is commonly used for several orthopedic procedures, including total knee arthroplasty and high tibial osteotomy. If a bone fragment in form of a piece of a first bone structure is sawn out to gain access for surgical treatment of a second bone structure, it is necessary that the bone be sawn precisely on the first try, so that the bone fragment, or bone segment, will fit precisely in place when put back and screwed in place. For better healing and alignment, the single saw cut is preferably a partial cut, not a through cut. It is also important that the drilling, or predrilling, of the fixation holes 410 is performed in a precise and reliable manner.

If a bone fragment in form of a piece of the lower tibia, or malleolus 300, is sawn out to gain access to the talus dome, it is necessary that the bone be sawn precisely on the first try, so that the bone fragment, or bone segment, will fit precisely in place when put back and screwed in place. For better healing and alignment, the single saw cut is preferably a partial cut, not a through cut. It is also important that the drilling, or predrilling, of the fixation holes is performed in a precise and reliable manner.

It is thus necessary to expose the talus dome by cutting out a portion of the lower medial tibia, under a number of difficult constrictions:
  avoiding all important tendons, muscles and ligaments and leaving them attached and intact,
  avoiding the anterior tibial artery,
  providing enough exposed space to correctly perform a surgical treatment of at least one of a bone and a cartilage damage of the talus dome,
  making the drilling of the fixation holes and the sawing of the bone cut precise and correct on the first try,
  facilitating a correct refixation of the temporarily removed bone fragment in form of a piece of the lower tibia, e.g. a piece of the malleolus, in its correct position for healing.

As regards to the above-mentioned aspect of facilitating the replacement and fixation of the bone fragment, the inventors have identified that it is increasingly important to provide for a more precise and reliable procedure for the predrilling past the bone fragment to be removed and into the bone there behind to thereby create fixation holes having the purpose of facilitating the correct refixation of the bone fragment after surgical treatment. If the at least one fixation hole is predrilled at a less desirable angle relative certain anatomic landmarks in a direction so that the at least one screw 420 is inserted either more horizontally or more vertically than optimal, an intra-articular step off might result. Vertical screw placement may also cause disruption of the deltoid ligament.

In order to obtain a congruent joint surface after fixation, the osteotomy cut is best directed perpendicular, or at least within an angle range of 60 to 90 degrees, to the articular surface of the tibia. An osteotomy which is too vertical or horizontal may result in an incongruent joint surface or shortening of the malleolus 300 after fixation. Furthermore, the fixation screws 420 should be directed essentially perpendicular, or within an angle range of 80-100 degrees, to the osteotomy plane.

The saw guide according to example embodiments is designed to achieve optimal compression and a congruent joint surface after surgical treatment of a damaged talus dome, i.e. when the removed bone fragment of a tibia is remounted, the at least one screw 420 needs to be inserted at a precise angle relative to e.g. the long tibial axis. As mentioned above, the osteotomy may then preferably be directed essentially perpendicularly, or at least within an angle range of 60 to 90 degrees, to the articular surface of the tibia at the intersection between the tibial plafond and medial malleolus. Furthermore, the fixation screws 420 should be directed essentially perpendicular, or within an angle range of 80-100 degrees, to the osteotomy plane.

According to a preferred method using the surgical kit and saw guide of the technology disclosed, the at least one screw hole 410, or fixation hole 410, is pre-drilled through the piece of the tibia and into the inner portions of the tibia, before the saw cuts are made to make sure that the tibia bone fragment will be remounted to its original, or substantially original, position. Certain aspects of the technology disclosed is aimed at providing the guiding tools facilitating a more precise saw cutting and a predrilling which are both performed in directions at desired, or optimal, angles relative certain anatomic landmarks of a patient, e.g. the long tibial axis.

In order to achieve optimal compression and a congruent joint surface after surgical treatment of the damaged talus dome, i.e. when the removed bone fragment of the tibia is remounted, the at least one screw 420 needs to be inserted at a precise angle relative to e.g. the long tibial axis. According to a preferred method using the surgical kit and saw guide of the technology disclosed, the at least one screw hole 410, or fixation hole 410, is pre-drilled through the piece of the tibia and into the inner portions of the tibia, before the saw cuts are made to make sure that the tibia bone fragment will be remounted to its original, or substantially original, position.

An example surgical kit according to the technology disclosed, which is suitable for repair of articular surfaces in the talocrural joint, comprises:
  a. A surgical implant having a cap with an outer surface conforming to a talus dome surface and an inner surface having a central implant anchoring peg extending perpendicularly from said inner surface,
  b. A drilling guide, conforming to a talus dome surface, comprising a hollow tubular shell 620 suitable for supporting vertical drilling into the dome,
  c. A saw guide 100 configured to conform to the lower portion of a tibia and comprising an opening 120 suitable for insertion of a cutting saw and directed at an angle providing for only one single saw cut and a single saw guide surface in one plane, wherein said saw guide, when conforming to the lower portion of the tibia, is configured to provide for saw cutting at an angle direction to the longitudinal axis of the tibia suitable for osteotomy of a lower portion of a tibia to expose the dome of the talus, thereby providing access for a surgeon implanting said surgical implant into the talar dome, and wherein said saw guide further comprises, as integral part, a drill guide 130 having at least one hole(s) 140 configured to guide and provide for drilling by a drilling tool at an angle direction which is within a range of 80-100 degrees to the saw cutting direction provided by said opening.

The above surgical kit may further comprise at least one screw(s) 420 which is adapted to be used for drilling through said drill hole(s) 410, said screw hole(s) having a shape, dimensions and a length adapted for drilling through and past the at least portion of the malleolus 300 to be removed and into the inner portions of the tibia before the single saw cut is made so that at least one hole remains in the inner portions of the tibia after removal of both the at least portion of the malleolus 300 and the saw guide 100, wherein a portion of the at least one hole 410 remaining in the inner portions of the tibia made by the drilling operation can be used for remounting the temporarily removed at least portion of the malleolus 300 in its original, or substantially original, position.

The above surgical kit may further be designed so that said saw guide is individually patient customized to conform to the lower portion of the tibia of a patient and is further configured so that the orthogonal direction to the plane of said opening for inserting a cutting saw is at an angle direction which is less than 45 degrees to the longitudinal tibial axis of the patient, thereby providing for said one saw cut through said at least portion of the malleolus 300 used for osteotomy of a lower portion of a tibia to expose the dome of the talus.

The above surgical kit may further be designed so that said saw guide is individually patient customized to conform to the lower portion of the tibia of a patient and further configured so that the saw cutting direction provided by said opening is at an angle direction within a range between 15 and 45 degrees to the longitudinal tibial axis of the patient, thereby providing for said one saw cut through said at least a portion of the malleolus used for osteotomy of a lower portion of a tibia to expose the dome of the talus.

The above surgical kit may further be designed so that said saw guide is individually patient customized to conform to the lower portion of the tibia of a patient and further configured so that the saw cutting direction provided by said opening is at an angle direction of 30 degrees to the longitudinal tibial axis of the patient, thereby providing for said one saw cut through said at least a portion of the malleolus used for osteotomy of a lower portion of a tibia to expose the dome of the talus.

The above surgical kit may further be designed so that at least a portion of the inner engagement surface 160 of said saw guide conforms to the lower medial anterior portion of the tibia. In certain aspects, the at least a portion of the inner engagement surface 160 of the saw guide is patient uniquely customized with a surface and dimensions designed to conform to the lower medial anterior portion of the tibia.

The surgical implant of the above surgical kit may be customized to an undamaged talus dome of a specific patient to be treated.

FIGS. 12 to 14 show the saw guide 100 of a kit according to the disclosure. In this example embodiment related to defects of the talar dome, each saw guide may be customized via imagery of the patient's tibia through e.g. MRI, CT or X-ray. The saw guide has a slit 120, or first opening 120, providing for a single saw cutting plane B. This example saw guide also has two pin holes 150 provided for securing the saw guide in place on the tibia. The portion 180 of the saw guide in FIG. 12 to 130 which comprises the saw cutting slit 120, and which may have dimensions corresponding to or defining the depth of the slit, may be designed with a depth or height which is adapted to a specific length of the sawblade 190 as the powertool 520, to which the sawblade is attached, engages and stops at the upper surface of this portion 180 of the saw guide 100. The portion 180 of the saw guide comprising said slit 120, or opening may be designed with a height that matches, or corresponds to, the length of the sawblade 190 to be used during sawing to thereby make the powertool 520 used during sawing stop against the top surface of the portion 180, thereby minimizing the risk of unintentionally sawing too far. In certain example embodiment of the method for designing the saw guide 100, the dimensions of the portion 180 of the saw guide may be customized, e.g. via imagery of the patient's bone structure through e.g. MRI, CT or X-ray and/or based on the sawblade selected.

According to certain aspects of this example embodiment illustrated in FIGS. 12 to 14, the saw guide may be individually made specific to the patient's specific anatomy and to the specific damage to the talus, possibly through the following saw guide design steps:

a. identifying a subchondral damage of the talus dome through radiological images such as MR, CT or X-ray images or through arthroscopy;

b. planning the size and the location of an osteotomy needed to get access to the talar dome to treat the damage;

c. creating a virtual 3D model of at least portions of at least one of the tibial bone and the talus bone from radiological images such as MR, CT or X-ray images; and d. virtually designing a patient specific osteotomy guide based on the 3D model and the size and location of the osteotomy needed.

According to certain of the example embodiment illustrated in FIGS. 12 to 14, the surgical saw guide 100 may be manufactured by a 3D printing process in which material is joined or solidified under computer control to create the surgical saw guide. The method of manufacturing by a 3D printing process may include building the surgical saw guide from computer-aided design (CAD) data by successively adding material layer by layer. The CAD data may further be based on a virtually designed patient specific osteotomy saw guide based on the 3D model of the at least portion of the first bone structure and the size and location of the osteotomy needed.

According to example embodiment, the above method of manufacturing the saw guide in a 3D printing process may preceded by the following steps of virtually designing a patient specific osteotomy saw guide:

a. identifying at least one of a bone and a cartilage damage of the second bone structure through radiological images such as MR, CT or X-ray images;

b. planning the size and the location of an osteotomy needed to get access to the second bone structure in the surgical treatment of said at least one of a bone and cartilage damage of the second bone structure;

c. creating a 3D model of at least a portion of at least one of the first and the second bone structure from radiological images such as MR, CT or X-ray images; and d. virtually designing a patient specific osteotomy saw guide based on the 3D model and the size and location of the osteotomy needed.

According to example embodiments, the technology disclosed proposes a method for designing a saw guide and a surgical method for use in osteotomy and the temporary osteotomic removal of a bone fragment of a first bone structure for exposing a portion of a second bone structure for treatment, comprising the steps of:

a. identifying at least one of a bone and a cartilage damage of the second bone structure through radiological images such as MR, CT or X-ray images;
b. planning the size and the location of an osteotomy of the first bone structure needed to get access to the second bone structure in the treatment, e.g. surgical treatment, of the at least one of a bone and cartilage damage of the second bone structure;
c. creating a virtual 3D model of at least a portion of at least one of the first and second bone structure from radiological images such as MR, CT or X-ray images;
d. designing a patient specific osteotomy saw guide based on the 3D model and the size and location of the osteotomy needed;
e. positioning and fixing the designed patient customized saw guide 100 so that the saw guide is conforming and fixable to the surface of the first bone structure;
f. making a saw cut along the saw guide surface excising a bone fragment in form of a piece of the first bone structure;
g. removing said bone fragment, or folding said bone fragment forward and outward preserving the attachment, and exposing the damaged area of the second bone structure;
h. performing treatment of said at least one of a bone and cartilage damage of the second bone structure; and
i. replacing said excised bone fragment into its original, or substantially original, position and fixing it in place.

With reference to the angle relationships and angles φ and β illustrated in FIGS. 15a and 15b and in example embodiments, the saw guide 100 of the technology disclosed can be designed with at least one hole 140 of an integrated drill guide 130 where the at least one hole 140 is configured to have an orientation adapted to guide the drilling at an angle β, or within an angle range, to the longitudinal tibial axis A of a patient, where the angle β, or angle range, is within the angle range of 50-70 degrees to the longitudinal tibial axis A of a patient. At least one the angles φ and β can be determined during the pre-operative planning stage of the osteotomy and may be determined in relation to other features, angle direction and surfaces of the saw guide or a patient. In certain aspects of the technology disclosed, the determination of at least one of the angles φ and β is individually patient customized on the basis of radiologically obtained patient data, such as MR, CT or X-ray imaging.

Figure 16A:
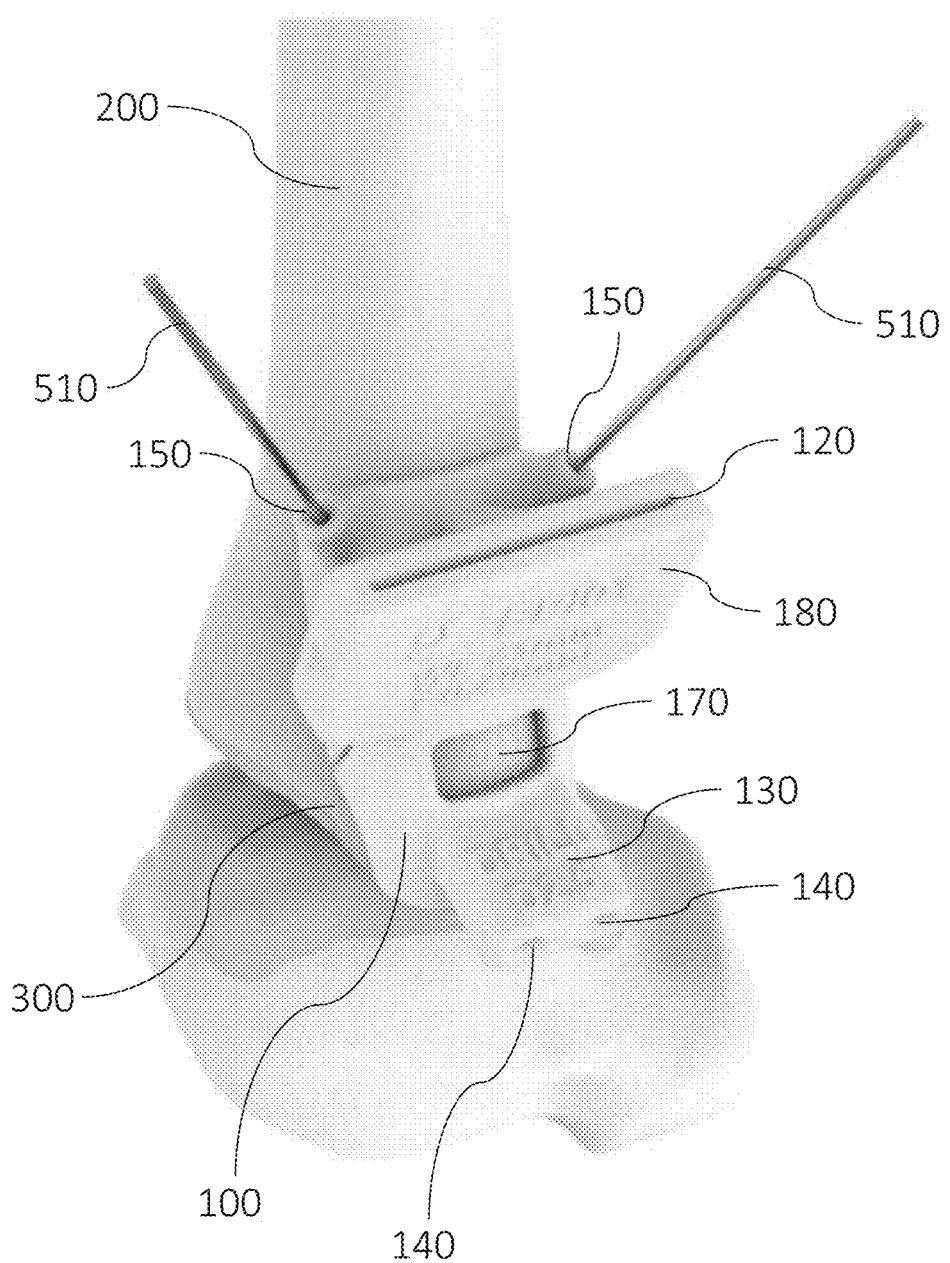
FIG. 16a shows a saw guide attached and secured to its position on the tibia, according to one or more embodiments of the technology disclosed.

FIG. 16a shows a saw guide 100, e.g. a talus osteotomy guide, in its unique position on the tibia. The saw guide 100 is attached and secured to the bone by inserting two pins 510 in the pin holes 150 on the proximal side of the saw guide.

Figure 16B:
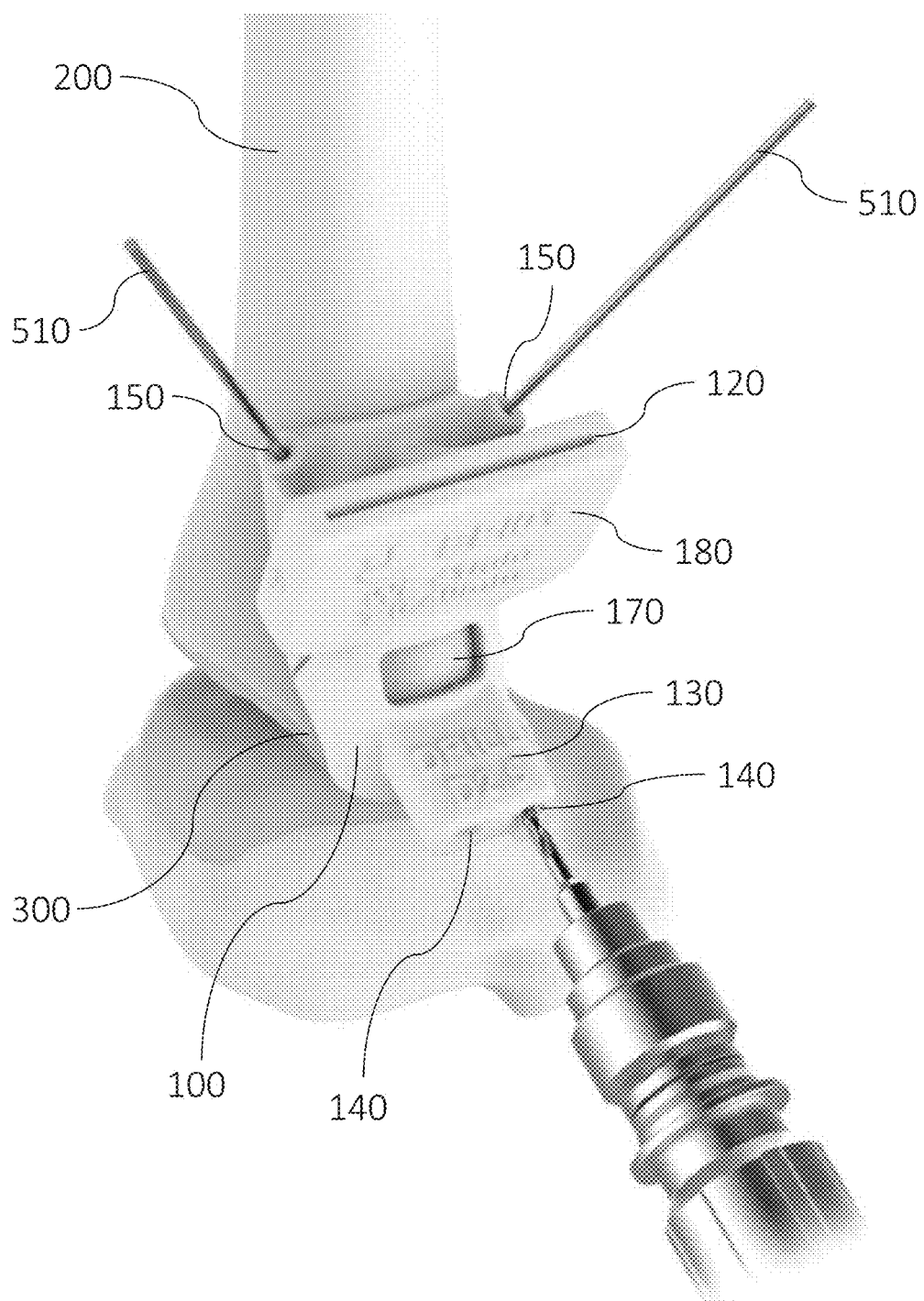
FIG. 16b shows the saw guide where the chuck and designated drill are attached to the power tool, for drilling of the drill holes, according to one or more embodiments.

FIG. 16b shows the saw guide 100 where the chuck and designated drill are attached to the power tool. The distal guiding holes 140 of the drilling guide 130 on the saw guide 100 are used for pre-drilling the fixation holes 410, or channels, which are used to refixate the temporarily removed bone fragment of the tibia after performing the surgical treatment of the talus.

Figure 16C:
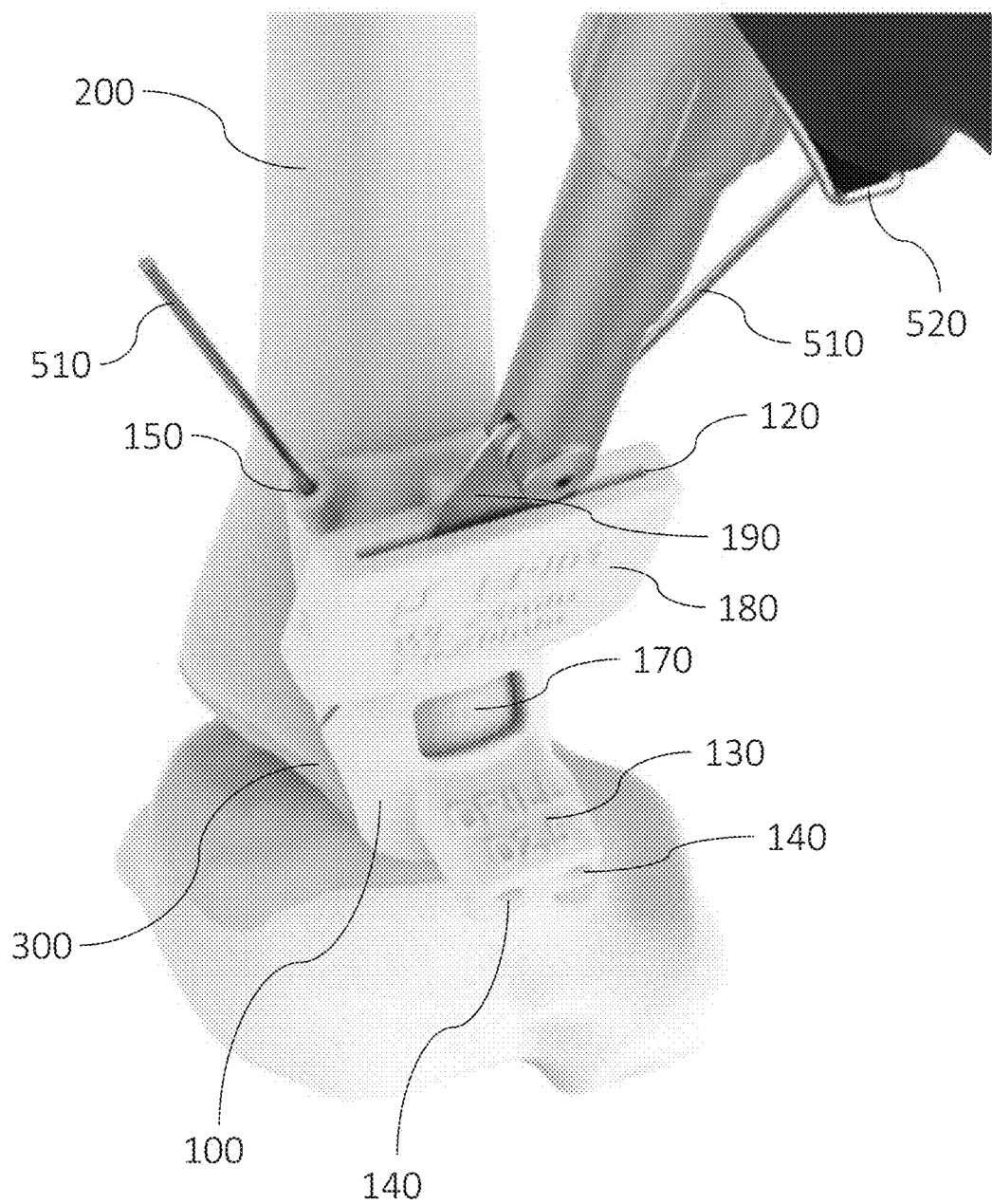
FIG. 16c shows the saw guide where a sagittal saw attachment and sawblade are attached to the powertool and the sawblade is inserted into the saw guide, according to one or more embodiments.

FIG. 16c shows the saw guide 100 where the sagittal saw attachment and sawblade 190 are attached to the powertool 520. The saw guide will guide the sawing and controls the depth of the cut. In certain aspects of the technology disclosed, the sawing will continue until the saw bottoms on the top of the saw guide.

Figure 16D:
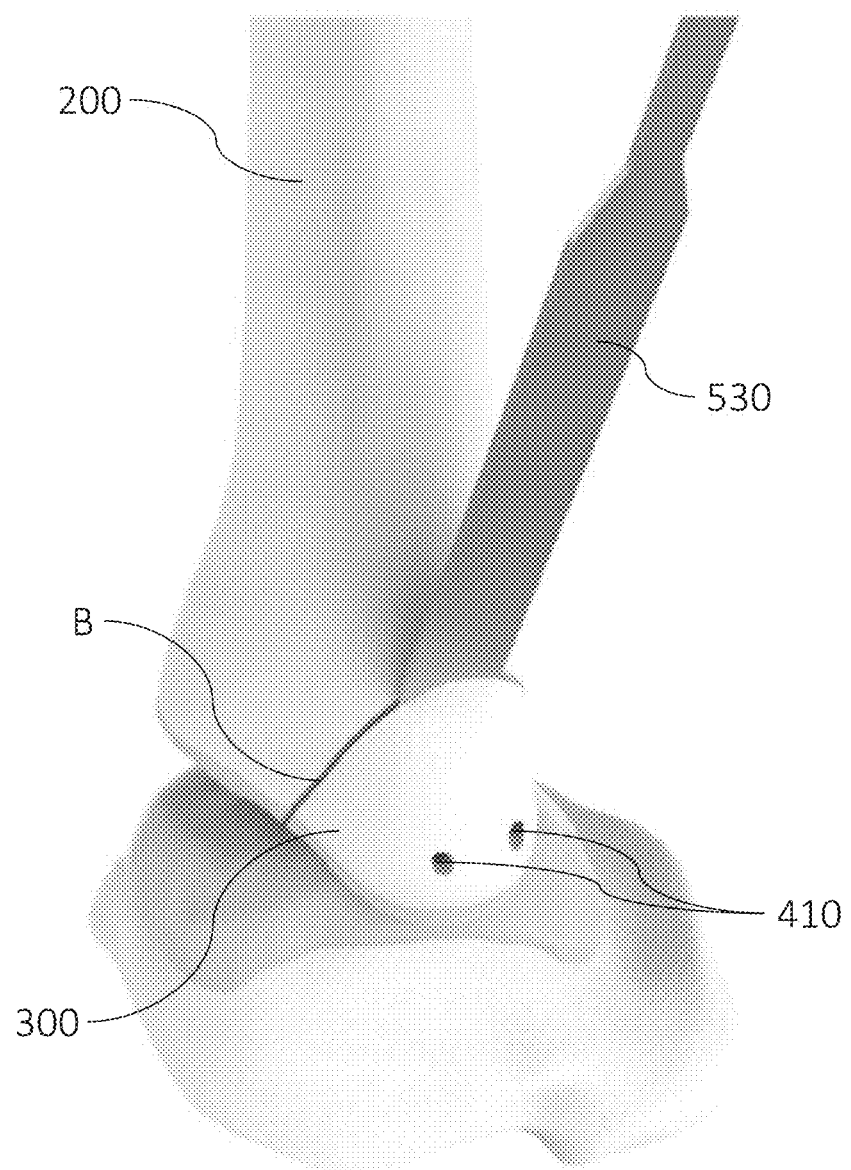
FIG. 16d illustrates a later stage in the osteotomic procedure when both the surgical pins and the saw guide have been removed, and an osteotome is applied for final loosening of the bone segment, according to one or more embodiments.

FIG. 16d illustrates a later stage in the osteotomic procedure when both the surgical pins 510 and the saw guide 100 have been removed. In this example, the osteotomy is continued by using an osteotome 530 to make sure to keep surrounding tissues away. In this example of procedure, a slight amount of bone is left intact to allow a final break-off by hand to reduce the risk of damaging the talus surface. This slight amount of bone left intact is then preferably broken off by hand and, as illustrated in FIG. 16d, a scalpel or chisel 530 is used to free the bone fragment of the last tibia adjoining tissue to remove the bone fragment in one piece, thereby providing temporary access to the dome of the talus for the surgeon to perform treatment such as e.g. surgical treatment.

Figure 17:
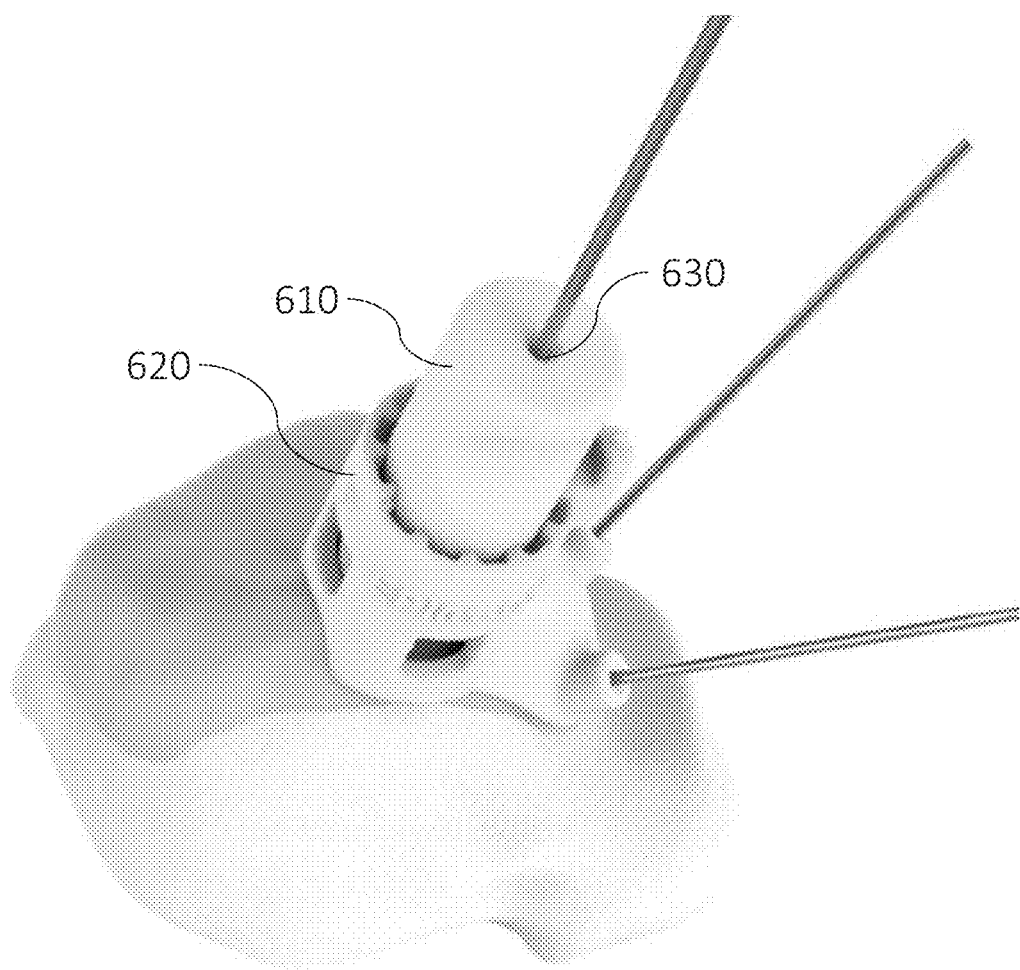
FIG. 17 shows a pin socket positioned in said hollow tubular shell, according to one or more embodiments of the technology disclosed.

FIG. 17 illustrates the pin socket 610 positioned in a hollow tubular shell 620. The pin socket 610 comprises a through hole in form of a steering hole 630. The pin socket, when positioned in said hollow tubular shell 620, provides mechanical support and the directional guidance for vertical drilling through said steering hole 630 and into the articular surface of a joint to form a steering hole in the articular surface of a joint for further drilling to remove cartilage and bone to prepare the site for implantation of an implant.

Figure 18:
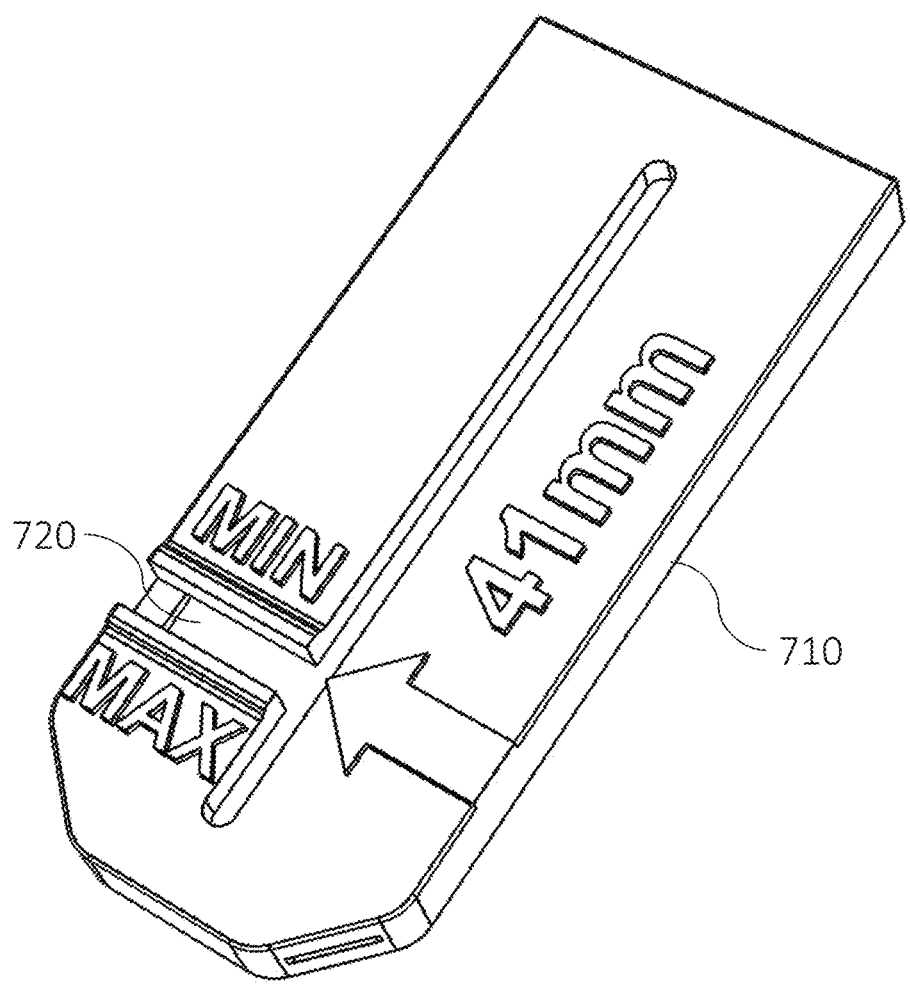
FIG. 18 shows a verification tool, or depth meter tool, for verifying that the correct sawblade has been selected, according to one or more embodiments.

FIG. 18 shows the depth meter verification tool 710. The verification tool 710, or depth meter tool, comprises a depth stop which is designed to be engaging a powertool used for the saw cutting procedure, a ta specific depth to prevent insertion of saw cutting blades into the slit 120 of the saw guide that cut beyond a certain length. In the verification process, the saw attachment and sawblade 190 are first attached to the powertool 520 and the depth meter 710 is used to verify that the selected sawblade has the correct dimension for the designed saw guide. The verification process selected sawblade 190 has the correct dimensions and length for the designed saw guide 100 using the depth meter verification tool 710 in FIG. 18 includes verifying that the tip of the sawblade 190 is visible within the MIN/MAX markings 720 of the depth meter verification tool.

Figure 19:
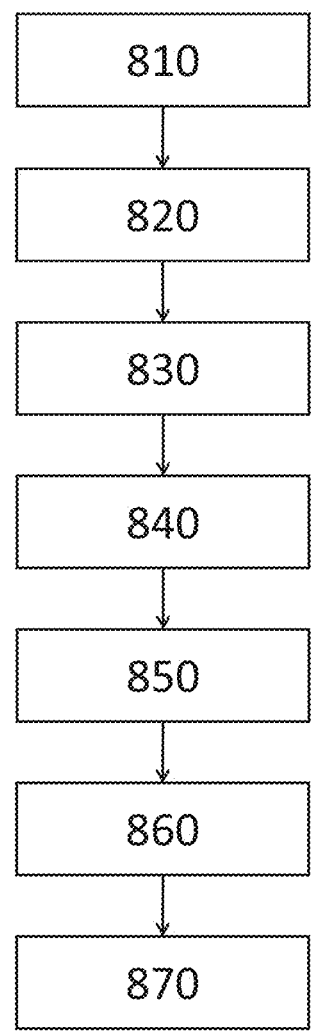
FIG. 19 is a process flow diagram showing the steps of an osteotomic procedure used, according to one or more embodiments of the technology disclosed.

FIG. 19 is a process flow diagram showing the steps of an osteotomic procedure used according to example embodiments of the technology disclosed, the example osteotomic procedure comprises at least a plurality of the following steps:

810: inserting at least one pin 510 in the at least one pin hole 150 on the proximal side of the saw guide 100 to secure the saw guide to the bone;

820: drilling the at least one fixation holes 410 by use of the directional guidance of the at least one hole 140 of the drill guide 130 of the saw guide 100;

830: attaching the saw attachment and sawblade 190 to a powertool 520 and inserting the sawblade 190 into the saw guide 100 to start sawing the saw cut;

840: removing the pins 510 and the saw guide 100 from the surgical field;

850: removing a bone fragment, or piece of the tibia, defined by the saw cut by breaking-off the bone fragment by the aid of an osteotome 530, e.g. a scalpel or chisel 530, to free the bone fragment of the last tibia adjoining tissue;

860: performing surgical treatment of the talar dome; and

870: refixating the removed bone fragment by use of fixation means 420 in form of e.g. screws which are screwed into the at least one fixation hole 410.

In certain embodiments of the above procedure and the technology disclosed, the cut out piece of the tibia bone, or malleolus, is not completely removed but is removed by still being attached to the tibia bone via the last tibia adjoining tissue and is only folded out when performing surgery treatment of the talar dome. After performed surgery, the cut out piece of the tibia is then folded back into its original, or substantially original, position and screwed into place preferably by the use of fixation means, e.g. by the use of two titanium screws.

According to example embodiments, the technology disclosed proposes a surgical method for use in osteotomy and the temporary osteotomic removal of a bone fragment of a tibia for exposing the talus dome for treatment, comprising the steps of:
1) identifying at least one of a bone and a cartilage damage of the talus dome through radiological images such as MR, CT or X-ray images;
2) planning the size and the location of an osteotomy needed to get access to the talus dome in the treatment of said at least one of a bone and a cartilage damage of the talus;
3) creating a virtual 3D model of at least a portion of at least one of the tibial bone and the talus bone from radiological images such as MR, CT or X-ray images;
4) designing a patient specific osteotomy saw guide based on the 3D model and the size and location of the osteotomy needed;
5) positioning and fixing the patient customized saw guide 100 so that the saw guide is conforming and fixable to the lower medial anterior portion of the tibia;
6) making a saw cut along the saw guide surface excising a lower medial anterior piece of the tibia;
7) removing said lower medial anterior piece, or folding said lower medial anterior piece forward and outward preserving the attachment of medial deltoid ligaments, and exposing the damaged condylar area of the talus dome;
8) performing treatment of said at least one of a bone and cartilage damage of the at least one of a bone and a cartilage damage of the talus; and
9) replacing said excised lower medial anterior piece of the tibia into its original, or substantially original, position and fixing it in place.

Certain aspects and embodiments of the technology disclosed the surgical procedure in which the kit and the saw guide of the disclosure are used could be defined in the following definitional points:

Method of joint implant surgery for repair of articular surfaces in the talocrural joint, comprising:
a) Fixing a patient customized saw guide (1) conforming and fixable to the lower medial anterior portion of the tibia and providing saw guide surfaces (2,3,4) in three different planes, suitable for osteotomy of a lower medial anterior piece of a tibia to expose the dome of the talus,
b) Making cuts along each of said three saw guide surfaces excising a lower medial anterior quadrant of the tibia,
c) Folding said lower medial anterior quadrant piece forward and outward, preserving the attachment of medial deltoid ligaments and exposing the damaged condylar area of the talus dome,
d) Mounting a patient customized form fitting hollow drill guide comprising a tubular shell in place on the talus dome, covering with its hollow part the damaged area of the talus to be repaired,
e) Drilling in said drill guide with a double drill having a narrow diameter deeper drill and a larger diameter shallower drill providing a bore for a talus implant,
f) Removing said drill guide,
g) Inserting into said bore a surgical implant (20) having a cap (21) with an outer surface (22) conforming to a talus dome surface and an inner surface having a central implant anchoring peg (23) extending perpendicularly from said inner surface,
h) Replacing said excised lower medial anterior quadrant piece into its original position and fixing it in place.

One Exemplary Surgical Procedure:

In the following one exemplary procedure is described for the use of the kit and the saw guide according to the disclosure. This description is of course not at all limiting of the invention. Rather other procedures may be used, for example with a block of the tibia removed with surfaces at other angles than the orthogonal angles described below. According to the technology disclosed, the patient customized saw guide only provides for a cut in one plane, e.g. for severing a portion of the malleolus, straight off, if, thereby only the medial portion of the talus dome need be exposed. The surgical saw guide can further be used for other treatments than the surgical implantation of implants according to certain embodiments of the present disclosure. The saw guide can for example be used for access to the talus dome for osteochondral treatment through biological procedures or for implantation of artificial plugs.

1. Incision: Wiberg surgical raspatory file. Hohmann retractors used to separate the skin after incision. White positioner.
2. A Hintermann distractor is used for separation.
    a. The patient customized saw guide is placed on the tibia after the bone has been exposed. Two 1.6 mm pins are inserted through pin holes in a form fitting flange on the saw guide and are driven into the tibia, holding the saw guide securely in place for all three orthogonal saw cuts to follow.
3. Two bore holes of 3.5-4 mm are first drilled through the intended osteotomic tibial quandrant and past the sagittal and coronal guide planes into the bone there behind. These holes are drilled at this time to assure exact replacement and fixation of the removed bone quadrant in its exact original position.
4. First the saw cuts in the transverse plane and in the coronal plane are made up to stop pins driven in to prevent cutting into the tibia beyond the quadrant block form to be removed.
5. A form fitting talus protector shield is slipped in anteriorly from between the talus dome and the malleolus and the lower condylar surface of the tibia, while avoiding the medial ligaments and the flexor digitorum longus and the tibialis posterior muscles. It is now possible to make the final cut in the sagittal plane without damaging the talus surface.
6. A flat and broad surgical chisel is used to remove any remaining bone holding the quadrant to the rest of the tibia.
7. The saw guide is removed.
8. The bone quadrant is pulled out and folded forward and downward all the while preserving the vital attachment of the medial (deltoid) ligaments to the removed tibia quadrant and to the calcaneus and the navicular.
9. The patient customized form fitting drill guide (Epiguide®) in the form of a tubular shell is mounted in place on the talus dome, covering with its hollow part the damaged area of the talus to be repaired. It extends with a saddle shaped mounting flange forward along the ridge of the talus. Pins through the mounting flange securely fix the drill guide to the talus.
10. The patient customized saw guide has assured that a bone quadrant has been sawn and removed in one try, which is large enough to provide access to the damaged area of the talus dome, to allow for vertical mounting and anchoring of the drill guide, to allow for vertical drilling into the talus through the drill guide, and to allow for hammering the implant into place in the drilled hole in the talus.

11. A drill sleeve is inserted into the drill guide. Cartilage is cut away and a double drill (12-17 mm/4 mm) is used to drill the deeper (4 mm diameter) hole for the peg and the shallow hole for the cap, which may have a slight peripheral rim on its underside.

12. A second drill sleeve (height adjustment sleeve) which is adjustable to the correct depth is inserted and fine-tuning of the drilling depth is performed.

13. A dummy implant (Epidummy®) with a handle and of slightly smaller diameter than the real implant (Episealer®) is inserted into the drilled double hole to check for correct depth and position of the hole. The dummy is then pulled out.

14. The drill guide is then removed.

15. The patient customized implant (Episealer®) is then pushed into place and then tapped finally into place using a mandril. The tibias quadrant piece which has been folded out exposes enough space within the tibia and above the talus dome to enable drilling for and insertion of the implant peg in the proper direction so that downward forces exerted by the tibia, when walking for example will be exerted largely in the direction of the peg so that no lateral forces will be exerted tending to dislodge the implant over time.

16. The excised tibia quadrant is then folded up into its original position and two screws screw it precisely into its original position by virtue of the fact that the deep screw holes were drilled into the intact tibia before the sawing operation.

17. The Hohmann skin retractors are removed and the tissue is sutured together.

Exemplary Surgical Procedures for Use Together with the Technology Disclosed

In the following one exemplary procedure is described for the use of the kit and the saw guide 100 according to the disclosure. This description is of course not at all limiting of the invention. Rather other procedures may be used, for example with a piece of the tibia removed with surfaces at other angles than the orthogonal angles described below. According to the technology disclosed, the patient customized saw guide only provides for a cut in one plane, e.g. for severing a portion of the malleolus, straight off, if, thereby only the medial portion of the talus dome need be exposed. The surgical saw guide can further be used for other treatments than the surgical implantation of implants according to certain embodiments of the present disclosure. The saw guide can for example be used for access to the talus dome for osteochondral treatment through biological procedures or for implantation of artificial plugs.

The osteotomy procedure may comprise at least a plurality of the following actions of a surgical treatment comprising the implantation of an implant into the dome of the talus:

1. The patient customized saw guide is placed on the tibia after the bone has been exposed. Two pins 510 are inserted through pin holes 150 on the saw guide 100 and are driven into the tibia 200, holding the saw guide securely in place for the single saw cut to follow.

2. Two bore holes 410 are first drilled through the intended osteotomic tibial piece and past the saw cutting plane B into the bone there behind. These holes 410 are drilled at this time to assure exact replacement and fixation of the removed bone fragment in its original, or substantially original, position.

3. A single saw cut, preferably not a through cut but a partial cut, is made in a saw cutting plane B.

4. An osteotome 530, e.g. in form of a flat and broad surgical chisel or scalpel, is used to remove any remaining bone holding the bone fragment to the rest of the tibia 200.

5. The saw guide is removed.

6. The bone fragment is pulled out and folded forward and downward all the while preserving the vital attachment of the medial (deltoid) ligaments to the removed tibia fragment and to the calcaneus and the navicular.

7. The patient customized saw guide has assured that a bone fragment has been sawn and removed in one try, which is large enough to provide access to the damaged area of the talus dome, to allow for surgical treatment of the talus, e.g. the vertical mounting and anchoring of a second drill guide, to allow for vertical drilling into the talus through the drill guide to prepare for an implant 8. Perform surgical treatment of at least one medial osteochondral defect of the talar dome. A drill sleeve may be used and inserted into the second drill guide. A drill, e.g. a double drill, may be used to drill the deeper hole for an implant peg and the shallow hole for the implant cap, which may have a slight peripheral rim on its underside.

9. A drill sleeve which is adjustable to the correct depth is inserted and fine-tuning of the drilling depth is performed.

10. A dummy implant is inserted into the drilled hole to check for correct depth and position of the hole. The dummy is then pulled out.

11. The drill guide is then removed.

12. The patient customized implant is then pushed into place.

13. After performed surgical treatment, the excised tibia fragment is then fixated, or folded up, into its original, or substantially original, position and two screws 420 are used for screwing the removed piece of the tibia, or malleolus, precisely into its original, or substantially original, position by virtue of the fact that the deep screw holes 410 were drilled into the intact tibia before the sawing operation.

In step 13 above, the patient customized implant may be pushed into place and then tapped finally into place using a mandrel. The cut out tibia piece which has been removed or folded out exposes enough space within the tibia and above the talus dome to enable drilling for and insertion of the implant peg in the proper direction so that downward forces exerted by the tibia, when walking for example will be exerted largely in the direction of the peg so that no lateral forces will be exerted tending to dislodge the implant over time.

The surgical kit according to the disclosure makes it possible to perform the above described surgical implant procedure which will make it possible to:

avoid all important tendons, muscles and ligaments and leaving them attached and intact, provide enough exposed space for medical treatment, e.g. a surgical treatment which includes correctly drill for and drive in the implant at the correct angle, make the bone cuts precise and correct on the first try, make possible precise reattachment of the tibia piece to its original, or substantially original, position for healing and correct alignment of the joint.

Certain aspects and embodiments of the technology disclosed the surgical procedure in which the kit and the saw guide of the disclosure are used could be defined in the following definitional points:

Method of joint implant surgery for repair of articular surfaces in the talocrural joint, comprising:
  i) Positioning and fixing a patient customized saw guide 100 so that the saw guide is conforming and fixable to the lower medial anterior portion of the tibia and is further providing a saw guide surface in one plane, thereby being suitable for osteotomy of a lower medial anterior piece of a tibia to expose the dome of the talus,
  j) Making a saw cut along the saw guide surface excising a lower medial anterior piece of the tibia,
  k) Removing said lower medial anterior piece, or folding said lower medial anterior piece forward and outward preserving the attachment of medial deltoid ligaments, and exposing the damaged condylar area of the talus dome,
  l) Mounting a patient customized form fitting hollow drill guide comprising a tubular shell in place on the talus dome, covering with its hollow part the damaged area of the talus to be repaired,
  m) Drilling in said drill guide with a double drill having a narrow diameter deeper drill and a larger diameter shallower drill providing a bore for a talus implant,
  n) Removing said drill guide,
  o) Inserting into said bore a surgical implant having a cap with an outer surface conforming to a talus dome surface and an inner surface having a central implant anchoring peg extending perpendicularly from said inner surface,
  p) Replacing said excised lower medial piece into its original, or substantially original, position and fixing it in place.

Certain Embodiments Related to Surgical Treatment and the Implantation of Metal Implants Implants having a top cap surface customized to each patient to replicate the surface of the talus dome before it was injured, must be implanted so that the forces, applied during standing and walking via the lower condylar surfaces of the tibia against the new implant will act axially in relation to the implantation peg, for optimum force absorption and length of life.

Because of the disadvantages of current secondary treatment methods for OCDs, metal resurfacing inlay implants have been developed and started to reach the market. A precise surgical technique is required in terms of implantation depth, position, and orientation because of the biomechanical properties of the ankle joint. A protruding implant may damage the opposite cartilage by causing excessive contact pressures during loading, which is thought to be due to "plowing" of the cartilage. On the other hand, a deep implant might result in collapse of the adjacent cartilage due to insufficient support.

The advantages of implants over complete replacement of the joint, see e.g. patent applications WO2014/020562 and US2010/0262150, have stimulated a further development of smaller implants that can be implanted with less invasive surgery. In this development, there has also been an effort to achieve small joint implants, suitable for repair of a small bone and/or cartilage injury that have a minimal influence on the surrounding parts of the joint. In the current development, such small implants are designed with an implant body that may be formed as a mushroom cap with a hard surface to face the articulating side of the joint and a bone contacting surface engaging the bone below the damaged part of cartilage. The shape and the curvature of the articulating surface of the implant may be designed to be a reconstitution of the shape and the curvature of the part of the joint when it was undamaged. Such implants are usually designed as mushrooms with an implant body or head and with a peg or a rod projecting from the bone contacting side of the implant body for anchoring the implant into the bone. The cap of the mushroom for repair of the talus dome is often slanted or irregular to conform to the shape of the original undamaged ridge or dome of the talus. The talar metal resurfacing implants preferably have an exact match to the undamaged talar anatomy.

The invention claimed is:

1. A surgical saw guide suitable for use in osteotomy and the temporary osteotomic removal of a distal portion of a tibia for exposing the talus dome for treatment, comprising:
  an inner engagement surface adapted to conform to at least a portion of the lower portion of the tibia;
  a slit configured to receive a saw cutting tool and to guide the saw cutting tool to form a single cut in a straight direction at an angle to at least a portion of the inner engagement surface of said saw guide for removal of the distal portion of a tibia, wherein said slit is further configured to guide the saw cutting tool to form a single osteotomy saw cut at an angle within the angle range of 15-50 degrees to the longitudinal tibial axis of a patient; and
  a drill guide having at least one hole configured to guide the drilling of a hole in a straight direction at an angle relative to the saw cutting direction provided by the guidance of said slit, wherein the at least one hole is configured to guide the drilling past a plane formed by the single saw cut and into inner portions of the tibia, wherein the inner portions of the tibia are portions remaining when the osteotomy is performed and the distal portion of the tibia is removed.

2. The surgical saw guide of claim 1, further comprising:
  at least one pin hole adapted to receive a fixation means to guide the temporary fixation of the saw guide to the tibia of a patient.

3. The surgical saw guide of claim 1, wherein said at least one hole of the drill guide is adapted to provide for the predrilling of at least one fixation hole in the inner portions of the tibia bone to be used for facilitating correct refixation of the removed distal portion of the tibia in its original, or substantially original, position after performed surgical treatment.

4. The surgical saw guide of claim 1, wherein said at least one hole of the drill guide is configured to guide the drilling along a straight line at a specific angle direction with respect to at least one of:
  the at least a portion of the inner engagement surface adapted to conform to the lower portion of the tibia of a patient,
  the longitudinal tibial axis of the patient, and
  the direction for forming said single saw cut.

5. The surgical saw guide of claim 4, wherein the at least one hole of said drill guide is configured to guide the drilling in a direction at an angle β or within an angle range to the longitudinal tibial axis of a patient, and wherein said angle β or angle range is within the angle range of 50-70 degrees to the longitudinal tibial axis of a patient.

6. The surgical saw guide of claim 4, wherein the at least one hole of said drill guide is configured to guide the drilling in a direction along a straight line at an angle β at 60 degrees, or close to 60 degrees, to the longitudinal tibial axis of a patient.

7. The surgical saw guide of claim 1, wherein the at least one hole of the drill guide is configured to guide drilling in a direction at an angle β or within an angle range to the direction for forming said single saw cut, and wherein said angle β or angle range is within the angle range of 80-100 degrees to the direction for forming said single saw cut.

8. The surgical saw guide of claim 1, wherein the at least one hole is configured to guide drilling in a perpendicular direction, or close to 90 degrees, with respect to the direction for forming said single saw cut.

9. The surgical saw guide of claim 1, wherein said inner engagement surface is adapted to conform to the lower portion of the tibia of a patient.

10. The surgical saw guide of claim 1, wherein said single saw cut has a pre-determined angle relationship to at least a portion of said inner engagement surface, and wherein said at least a portion of said inner engagement surface is patient customized to be adapted to conform to the lower portion of the tibia of a patient.

11. The surgical saw guide of claim 1, wherein said slit is further configured to guide a saw cutting tool to form a single saw cut in a direction at an angle of 30 degrees, or close to 30 degrees, to the longitudinal tibial axis of a patient.

12. The surgical saw guide of claim 1, further comprising:
an opening which forms an inspection window adapted to allow visual inspection of how well the saw guide conforms to the lower portion of the tibia of a patient to facilitate adjustment of the positioning of the saw guide to provide for a correct positioning of the saw guide to the lower portion of the tibia of the patient.

13. The surgical saw guide of claim 1, wherein a portion of the saw guide comprising said slit is configured to have a height that matches, or corresponds to, the length of a sawblade to be used during saw cutting to make a powertool used during saw cutting stop against the top surface of the portion.

14. A method for designing the surgical saw guide according to claim 1, comprising:
designing a saw guide having as integral parts both a slit designed for guiding the saw cutting in a first direction and a drill guide having at least one hole designed for guiding the drilling in a second direction different from the first direction.

15. The method of claim 14, wherein the at least portion of the inner engagement surface is adapted to conform to the lower portion of the tibia of a patient and is individually patient customized on the basis of radiologically obtained patient data.

16. The method of claim 14, wherein the at least one hole of the drill guide is individually patient customized on the basis of radiologically obtained patient data in that the drilling direction provided by said at least one hole is designed to have a patient customized angle relationship to at least one of the lower portion of the tibia of a patient and the longitudinal tibial axis of the patient.

17. The method of claim 14, wherein the slit is individually patient customized on the basis of radiologically obtained patient data in that the saw cutting direction provided by said slit is designed to have a patient customized angle relationship to at least one of the lower portion of the tibia of a patient and the longitudinal tibial axis of the patient.

18. The method of claim 14, wherein both the slit and the at least one hole of the drill guide are individually patient customized on the basis of radiologically obtained patient data in that both the saw cutting direction provided by said slit and the drilling direction provided by the at least one hole of the drill guide are each designed to have a patient customized angle relationship to at least one of the lower portion of the tibia of a patient and the longitudinal tibial axis of the patient.

19. A surgical kit comprising:
the saw guide according to claim 1; and
fixation means with dimensions adapted for insertion through the at least one hole of the drill guide and having a certain length for providing fixation of the saw guide to the tibia by use of the at least one fixation hole in the inner portions of the tibia,
wherein said surgical kit is designed to provide for the remounting of the temporarily removed distal portion of the tibia in its original, or substantially original, position by using the pre-drilled at least one hole in the inner portions of the tibia.

20. The surgical kit of claim 19, wherein said fixation means includes at least a screw designed to be screwed through and past the distal portion of the tibia to be removed and into a pre-drilled fixation hole in the inner portion of the tibia bone, and wherein said fixation means is configured to provide for the remounting of the temporarily removed distal portion of the tibia in its original, or substantially original, position by using the pre-drilled at least one fixation hole in the inner portions of the tibia.

21. The surgical kit of claim 19, further comprising a surgical implant having a cap with an outer surface conforming to a talus dome surface and a hollow tubular shell suitable for vertical drilling to prepare the talus dome for implantation of an implant.

22. The surgical kit of claim 21, further comprising a pin socket adapted to be positioned in said hollow tubular shell and which is configured with a steering hole in the form of a through hole, wherein said pin socket, when positioned in said hollow tubular shell, provides mechanical support and the directional guidance for vertical drilling through said steering hole and into the dome of the talus to form a steering hole in the dome of the talus for further drilling to remove cartilage and bone to prepare the site for implantation of an implant of the talus dome.

23. A surgical kit comprising:
the saw guide according to claim 1; and
a surgical implant having a cap with an outer surface conforming to a talus dome surface and a hollow tubular shell suitable for providing support to the vertical drilling to prepare the talus dome for implantation of an implant.

24. The surgical kit of claim 23, further comprising a pin socket adapted to be positioned in said hollow tubular shell and which is configured with a steering hole in the form of a through hole, wherein said pin socket, when positioned in said hollow tubular shell, provides mechanical support and the directional guidance for vertical drilling through said steering hole and into the dome of the talus to form a steering hole in the dome of the talus for further drilling to remove cartilage and bone to prepare the site for implantation of an implant of the talus dome.

25. The surgical kit of claim 23, further comprising at least one fixation means designed with dimensions and a length adapted for insertion of said fixation means through the at least one hole of the drill guide and to provide fixation of the saw guide to the tibia and having a certain length adapted to enable insertion into the at least one fixation hole into the inner portions of the tibia,
wherein said surgical kit is designed to provide for the remounting of the temporarily removed distal portion of the tibia in its original, or substantially original, position by using the pre-drilled at least one hole in the inner portions of the tibia.

26. A method of manufacturing the surgical saw guide according to claim 1, comprising 3D printing by joining or solidifying material under computer control to create the surgical saw guide.

27. The method of manufacturing of claim 26, wherein said 3D printing includes building the surgical saw guide from computer-aided design (CAD) data by successively adding material layer by layer.

28. The method of manufacturing of claim 27, wherein the CAD data is based on a virtually designed patient specific osteotomy saw guide based on the 3D model of the at least portion of the first bone structure and the size and location of the osteotomy needed.

29. The method of manufacturing of claim 28, wherein the 3D printing is preceded by the following steps of virtually designing a patient specific osteotomy saw guide:
 a. identifying at least one of a bone and a cartilage damage of the second bone structure through radiological images;
 b. planning the size and the location of an osteotomy of a first bone structure needed to get access to the second bone structure in the treatment of said at least one of a bone and cartilage damage of the second bone structure;
 c. creating a virtual 3D model of at least a portion of at least one of the first and second bone structure from radiological images; and
 d. designing a patient specific osteotomy saw guide based on the 3D model and the size and location of the osteotomy needed.

* * * * *